(12) United States Patent
Banerjee

(10) Patent No.: US 8,003,572 B2
(45) Date of Patent: Aug. 23, 2011

(54) METHOD FOR THE TREATMENT OF A UBIQUITIN CONJUGATING DISORDER

(75) Inventor: Amit Banerjee, Grosse Pointe, MI (US)

(73) Assignee: Amit Banerjee, Grosse Pointe, MI (US)

( * ) Notice: Subject to any disclaimer, the term of this patent is extended or adjusted under 35 U.S.C. 154(b) by 302 days.

(21) Appl. No.: 11/647,788

(22) Filed: Dec. 28, 2006

(65) Prior Publication Data

US 2007/0191488 A1    Aug. 16, 2007

Related U.S. Application Data

(62) Division of application No. 10/914,848, filed on Aug. 10, 2004.

(51) Int. Cl.
*C40B 30/02* (2006.01)
*C12N 9/10* (2006.01)

(52) U.S. Cl. ............................. 506/8; 435/193

(58) Field of Classification Search ................. None
See application file for complete search history.

(56) References Cited

U.S. PATENT DOCUMENTS

| | | | |
|---|---|---|---|
| 5,272,157 A | 12/1993 | George et al. | |
| 5,981,699 A * | 11/1999 | Draetta et al. | 530/350 |
| 5,985,857 A | 11/1999 | Hudson et al. | |
| 6,544,997 B1 | 4/2003 | Bosmans et al. | |

OTHER PUBLICATIONS

Rolfe et al. ("Reconstitution of p53-ubiquitinylation reactions from purified components: The role of human ubiquitin-conjugating enzyme UBC4 and E6-associated protein (E6AP)," Proc. Acad. Sci. USA, 1995, 92, 3264-8.*

Hamilton et al. ("Structure of a Conjugating Enzyme-Ubiquitin Thiolester Intermediate Reveals a Novel Role for the Ubiquitin Tail," Structure, 2001, 9, 897-904).*
Lyne ("Structure-Based Virtual Screening: An Overview," Drug Discovery Today, 2002, 7, 1047-1055).*
Scheffner et al. ("Identification of a human ubiquitin-conjugating enzyme that mediates the E6-AP-dependent ubiquitination of p53," Proc. Natl. Acad. Sci., 1994, 91, 8797-8801).*
Sadowski ("Tautomer and protonation pre-processor virtual screening," Abstract of Papers, 224th ACS National Meeting, Boston, MA, Aug. 18-22, 2002).*
Pearlman et al. ("ProtoPlex: user-control over tautomeric and protonation state," Abstract of Papers, 224th ACS National Meeting, Boston, MA, Aug. 18-22, 2002).*
Hershko, A., and Ciechanover, A.(1992) Ann Rev Biochem 61: 761-807. The ubiquitin System for protein degradation.
Goettsch, S. and Bayer, P.(2002) Frontiers in Bioscience, 7, a148-162. Structural attributes in the conjunction of Ubiquitin, RUB and SUMO to protein substrates. Hershko, et al. J. Biol. Chem., 269:4940-46.
"Overexpression of E2F-1 in Lung and Liver Metastases of Human Colon Cancer is Associated with Gene Amplification", Iwamoto, et al. Cancer Biol Ther. Apr. 2004; 3(4):395-399.
"UbcH10 is the Cancer-related E2 Ubiquitin-conjugating Enzyme" Okamoto, et al. Cancer Res. 2003 63(14): 4167-73.
Shirahata A. et al, Enzymatic aminopropylation of certain secondary amines. Biol.Pharm.Bull. Feb. 1995; 18(2):355-9.
International Search Report for PCT/US05/28358 dated Sep. 21, 2006.

* cited by examiner

*Primary Examiner* — Christina Bradley

(57) ABSTRACT

The present invention provides methods for identifying compounds that selectively bind one or more active sites within an ubiquitin conjugating enzyme. The compounds identified by the methods are useful in the treatment of disorders attributed to dysregulated ubiquitin conjugating enzyme function, specifically in hyperproliferative disorders.

14 Claims, 6 Drawing Sheets

METHOD FOR THE TREATMENT OF A UBIQUITIN CONJUGATING DISORDER

RELATED APPLICATIONS

This application is a divisional application of U.S. application Ser. No. 10/914,848, filed on Aug. 10, 2004. The entire teachings of the above application is incorporated herein by reference.

GOVERNMENT SUPPORT

The invention was supported, in whole or in part by a grant NIH R01-GM59467 from the National Institutes of Health. The Government has certain rights in the invention.

BACKGROUND

The ubiquitin system is the major pathway for the controlled degradation of intracellular proteins in eukaryotic cells. The ubiquitin system regulates the half-life of cellular proteins including, cyclins, cyclin dependent kinase inhibitors, histones, oncoproteins and tumor suppressors and is an important regulatory component of cell cycle progression, endocytosis, receptor regulation, transcription, signal transduction, oncogenesis, apoptosis and antigen presentation (Hershko et al., *J. Biol. Chem.*, 269:4940-46). Abnormalities in the ubiquitin pathway are implicated in many pathological conditions including cancer (Johnston, 1999).

In the ubiquination pathway targeted proteins are marked with a chain of four or more ubiquitins that are covalently attached through the formation of an isopeptide bond between the C-terminal glycyl residue of ubiquitin and a specific lys1 residue in the substrate protein. The chain of ubiquitins mark the protein for degradation by a multi-subunit ATP-dependent protease known as the 26S proteasome enzyme complex. The degradation process is catalyzed in a sequential reaction involving three enzymes: E1 a ubiquitin activating enzyme, E2 an ubiquitin-conjugating enzyme, and E3 an ubiquitin-protein ligase enzyme. E1, in an ATP dependent process, forms a thiol ester bond with the C-terminus of ubiquitin. The activated ubiquitin is then transferred to a catalytic cysteine on one of several E2 enzymes. The E2 then donates the ubiquitin directly to the protein substrate or by association with an E3 protein (ubiquitin ligase; in most cases a polyprotein complex). After ligation of the first ubiquitin to the substrate protein, further ubiquitins are usually targeted to the first ubiquitin to form multi-ubiquitin chains. The 26S proteasome then catalyzes the degradation of the ubiquitin tagged proteins. Disruptions in the regulation of protein degradation by the ubiquitin pathway can significantly impact pathways in which correct protein concentration and half-life are essential, e.g., cell cycle.

Thus, defects in the ubiquitin pathway are likely to cause excessive proliferation and transformation in cells and thus inhibitors of this pathway are needed. However, because the ubiquitin pathway plays an essential role in many biological pathways, non-selective compounds are likely to be toxic. Thus, targeting specific ubiquitin enzymes may overcome the obstacle of toxicity. An attractive target in this pathway are the E2, ubiquitin conjugating enzymes. However, there are currently no compounds that selectively target E2. Thus there is a need in the art to develop safe and effective compounds that selectively inhibit ubiquitin conjugating enzymes or E2s.

SUMMARY OF THE INVENTION

The present invention to provide methods for identifying compounds that selectively bind one or more domains of the active sites within an ubiquitin conjugating enzyme and inhibit its activity. These compounds of the invention are useful in the treatment of ubiquitin conjugation associated disorders, particularly hyperproliferative disorders.

In one aspect, the present invention provides a method for inhibiting an ubiquitin conjugating enzyme with an organic compound with a molecular weight of less than about 2000 daltons, the method comprising selectively targeting to one or more active sites of the ubiquitin conjugating enzyme with the compounds. Preferably, the molecular weights of the organic compounds of the invention are less than about 2000 daltons, and more preferably, less than about 500 daltons. In one embodiment of the invention, the selectively targeted active site is within the catalytic site.

In another embodiment, the organic compound binds to a binding domain in an E1 binding site on the ubiquitin conjugating enzyme. In another embodiment, the ubiquitin conjugating enzyme is Ubc1, Ubc2, Ubc3, Ubc4, Ubc5, Ubc6, Ubc7, Ubc8, Ubc10, Ubc13. In a further embodiment, the ubiquitin conjugating enzyme is a yeast ubiquitin conjugating enzyme or a mouse, rat or human homolog.

In different embodiments of the invention, the compounds of the invention selectively target one or more active sites of the ubiquitin conjugating enzyme, including the following: amino acid residues corresponding to Lys64, Pro66, Lys67, Ile68, Asn84, Ile85, Leu90, Lys91Lys91 and Leu120 of SEQ ID NO:1; amino acid residues corresponding to Pro65, Pro66, Lys67, Ile68, Asn84, Leu90, Lys91 and Leu120 of SEQ ID NO:1; amino acid residues corresponding to Lys66, Ile67, Ala68, Ser83, Cys85, Leu86, Leu89 and Arg90 of SEQ ID NO:2; amino acid residues corresponding to Pro64, Pro65, Lys66, Ile67, Ser83, Ile84, Cys85, Leu86, Leu89, Arg90 and Leu119 of SEQ ID NO:2; amino acid residues corresponding to Pro68, Lys70, Tyr83, Glu87, Val88, Cys89, Leu93 and His94 of SEQ ID NO:3; and amino acid residues corresponding to Pro68, Pro69, Lys70, Leu71, Tyr83, Glu87, Val88, Cys89, Leu93 and His94 of SEQ ID NO:3.

In further embodiments of the invention, the compounds of the invention selectively targets one or more binding domains within the active sites, including the following: amino acid residues corresponding to Pro66, Ile85 and Leu90 of SEQ ID NO:1; amino acid residues corresponding to Pro66, Ile68, Leu90 and Lys91 of SEQ ID NO:1; amino acid residues corresponding to Ile67 and Leu89 of SEQ ID NO:2; amino acids corresponding to Pro65, Ile67, and Ser 83 of SEQ ID NO:2; amino acids corresponding to Glu87, Val88, Leu93 and His94 of SEQ ID NO:3; and amino acids corresponding to Pro69, Leu71 and Val88 of SEQ ID NO:3.

In one embodiment, the present invention provides a selective ubiquitin conjugating enzyme inhibitors of formula (I):

$$Ar—B—NR_1R_2 \qquad (I)$$

wherein:

Ar is a five or six membered unsubstituted or substituted aromatic ring that is optionally fused to an aromatic or heteroaromatic ring;

B is a bond, CO, $SO_2$ or $(CH_2)_n$ wherein n=1-5; and $R_1$ and $R_2$ are each independently H, alkyl or aryl groups that are optionally substituted;

wherein the Formula I compound selectively binds to one or more catalytic domains in the ubiquitin conjugating enzyme. Preferably, Ar is phenyl, pyridyl, napthyl, triazine, triazole, quinoxaline, dibenzofuran, benzimidazole, indene, indeno oxadiazine, indazole or an indole ring; B is a bond, CO or $(CH_2)_n$ wherein n=1; and $R_1$ and $R_2$ are both H.

In a preferred embodiment, the formula I compound is 3-amino-1,2,4-Triazine, 3-amino-1,2,4-triazole, 2-methyl-4-nitroaniline, 2-iodo-4-nitroaniline, 4-amino-3-chloro-5-methylbenzoic acid, 1-(4'Aminophenyl)-1,2,4-triazole, 2-acetamidophenol, 5-chloro-2,3-dihydroxypyridine, 2-methyl-3-(1H-pyrazol-5-yl)imidazo(1,2-a)pyridine, 5-nitro-2,3-dihydro-1H-benzo(d)imidazol-2-one, 4-(methylamino)pyridine, 2-Chloro-4-nitrobenzamide, 2-ethylformanilide, 6-aminoindazole, 2,3-diaminobenzoic acid, 1-(5-chloro-2-methylphenyl)-2-thiourea, 4,5-diiodo-1H-imidazole, 1H-indene-1,3(2H)-dione 1-methylhydrazone, 3-hydroxyindole, 3,4-dihydro-1H-quinoxalin-2-one, 1S,6S,7R,8R,8aR)-1,6,7,8-Tetrahydroxyoctahydroindolizidine, 2-naphthalen-1-yl-2,3-dihydro-1H-pyrimidine, benzo(b)thiophen-3-ylmethylamine, 1-allyl-2-4-dioxo-1-2-3-4-tetrahydro-5-pyrimidinecarbonitrile, Methyl(S)—N-(7-chloro-2,3,4a,5-tetrahydro-4a-(methoxycarbonyl)indeno(1,2-e)(1,3,4)oxadiazin-2-ylcarbonyl)-4'-(trifluoromethoxy)carbanilate (Indoxacarb-MP), and 4-acetylpyridine and thioisonicotinamide.

In a currently preferred embodiment, the formula I compound of the invention is 4-(Aminomethyl)piperidine. Typically, the formula I compounds of the invention have a molecular weight of less than about 2000 daltons, and preferably, a molecular weight of less than about 500 daltons.

In another embodiment, the present invention provides a selective ubiquitin conjugating enzyme inhibitor of formula (II):

$$A\text{-}(B\text{—}NR_1R_2)_n \quad (II)$$

wherein:
A is a 3-6 membered substituted or unsubstituted cycloaliphatic or a heterocycloaliphatic ring, each of which is optionally fused to an aromatic ring;
B is a bond, CO, $SO_2$ or $(CH_2)_n$ wherein n=1-3; and
$R_1$ and $R_2$ are each independently H, alkyl or aryl groups that are optionally substituted, and the compound selectively binds to one or more catalytic domains in the ubiquitin conjugating enzyme.

Preferably, the A of the compound of formula II is a heterocycloaliphatic ring comprising, at least one nitrogen atom and optionally, one or more additional heteroatoms selected from the group consisting of: nitrogen (N), oxygen (O) and sulfur (S); B is a bond, CO or $(CH_2)_n$ wherein n=1; and $R_1$ and $R_2$ are both H. In another embodiment of the invention, the cycloaliphatic or heterocycloaliphatic ring of formula II comprise one or more substituents selected from the group consisting of hydroxyl, halogen, CO and alkyl.

In a preferred embodiment, the formula II compound of the invention is 1-phenyl-4-methyl-3-pyrazolidone, 4-(aminomethyl)piperidine, N-Phenyl-p-phenylenediamine, 5-(aminomethyl)-3-(2H)-isoxazolone (Muscimol), (R)-2-aminomethylpyrrolidine, 2-pyrrolidinone oxime and 1-cyclopropylethylamine.

The formula II compounds of the invention typically have a molecular weight of less than about 2000 daltons, and preferably, a molecular weight of less than about 500 daltons.

In another embodiment of the invention, the organic compound is an aromatic or heteroaromatic compound comprising a piperidinyl, phenyl, quinolinyl and isoquinolinyl ring and having one or more nitrogen containing substituents selected from the group consisting of $NR_3R_4$, $(CH_2)_nNR_3R_4$, $CONH_2$, NH—NH—$R_5$ and C(S)—NH—$R_6$, wherein $R_3$, $R_4$, $R_5$ and $R_6$ are independently H, alkyl, cycloalkyl and aryl, and n is 1-5, and the compound selectively interacts with the E1 binding site of the ubiquitin conjugating enzyme. In further embodiment of the invention, the aromatic or heteroaromatic compound is 4-methylcyclohexylamine, 3-(dimethylamino)-1-(5-fluoro-2-hydroxyphenyl)prop-2-en-1-one, 3-ethoxyphenethylamine, 4-fluorobenzenesulfonamide, 2-((4-fluorophenyl)-hydrazono)malononitrile, 3-fluoro-4-hydroxybenzaldehyde or 1-aminoisoquinoline. In still another embodiment of the invention, the aromatic or heteroaromatic compound is less than about 2000 daltons. In another embodiment, the compound the aromatic or heteroaromatic compound is less than about 500 daltons.

In still another embodiment of the invention, the organic compound is a 7 or 8 membered monocyclic or bridged bicyclic compound with a cycloheptyl, cyclooctyl, and bicyclo(2,2,1) heptenyl having one or more substituents selected from the group consisting of $NR_3R_4$, $(CH_2)_nNR_3R_4$, $CONH_2$, NH—NH—$R_5$ and C(S)—NH—$R_6$, wherein $R_3$, $R_4$, $R_5$ and $R_6$ are independently H, alkyl, cycloalkyl and aryl, and n is 1-5, and the compound selectively interacts with the E1 binding site of the enzyme. In a further embodiment of the invention, the 7 or 8-membered monocyclic or bridged bicyclic compound is 6,7-dihydro-5H-dibenzo(a,c)cycloheptene-6-carboxylic acid, N-bicyclo(2.2.1)hept-5-en-2-ylthiourea, or N1-cyclooctyl-4-hydroxy-1-piperidinecarbothioamide.

Typically, the 7 or 8-membered monocyclic or bridged bicyclic compound of the invention has a molecular weight of less than about 2000 daltons, and preferably, less than about 500 daltons.

In another aspect of the invention, a method is disclosed for determining a selective interaction between a ubiquitin conjugating enzyme and an organic compound. The method includes the steps of inputting 3-D co-ordinates of at least a fragment of the ubiquitin conjugating enzyme into an electronic storage medium, determining one or more active sites in the fragment, modifying a library of organic compounds to have hydrogens creating a modified library of organic compounds, simulating a binding interaction between the active sites in the fragments and the modified library of organic compounds, and identifying compounds in the modified library of organic compounds that interact with the active sites in the fragments.

In yet another aspect of the invention, a method is disclosed for determining a selective interaction between a ubiquitin conjugating enzyme and an organic compound. The method includes the steps of inputting 3-D co-ordinates of at least a fragment of the ubiquitin conjugating enzyme into an electronic storage medium, determining one or more active sites in the fragment, simulating a binding interaction between the active sites in the fragments and a library of organic compounds, and identifying compounds in the library of organic compounds that interact with the active sites in the fragments. In another embodiment of the invention, the ubiquitin conjugating enzyme is selected from the group consisting of: Ubc1, Ubc2, Ubc3, Ubc4, Ubc5, Ubc6, Ubc7, Ubc8, Ubc10, Ubc11 and Ubc13. In a further embodiment, the ubiquitin conjugating enzyme is a yeast ubiquitin conjugating enzyme or a mouse, rat or human homolog. In another embodiment, the 3-D coordinates are 1AYZ, 1A3S, 1QCQ, 2UCZ, 1I7K 1J7D, 1JAT, 1JBB and variants thereof. In another embodiment, a molecular topology and charge visualization program performs the step of determining one or more active sites. In a further embodiment, the molecular topology and charge visualization program is the InsightII or Weblab Viewer programs. In another embodiment, the step of simulating a binding interaction is performed with the LUDI program. In a further embodiment, the library of organic compounds is the Available Chemicals Directory.

In yet another embodiment, the present invention provides compounds and methods for selectively targeting the active site in the ubiquitin conjugating enzyme comprising amino acid residues corresponding to Lys64, Pro66, Lys67, Ile68, Asn84, Ile85, Leu90, Lys91 and Leu120 of SEQ ID NO:1. In another embodiment, the active selectively targeted site comprise amino acid residues corresponding to Pro65, Pro66, Lys67, Ile68, Asn84, Leu90, Lys91 and Leu120 of SEQ ID NO:1. In another embodiment of the invention, the selectively targeted active site comprises the amino acid residues corresponding to Lys66, Ile67, Ala68, Ser83, Cys85, Leu86, Leu89 and Arg90 of SEQ ID NO:2. In another embodiment of the invention, the selectively targeted active site comprises the amino acid residues corresponding to Pro64, Pro65, Lys66, Ile67, Ser83, Ile84, Cys85, Leu86, Leu89, Arg90 and Leu119 of SEQ ID NO:2. In another embodiment of the invention, the selectively targeted active site comprises the amino acid residues corresponding to Pro68, Lys70, Tyr83, Glu87, Val88, Cys89, Leu93 and His94 of SEQ ID NO:3. In another embodiment of the invention, the selectively targeted active site comprises the amino acid residues corresponding to Pro68, Pro69, Lys70, Leu71, Tyr83, Glu87, Val88, Cys89, Leu93 and His94 of SEQ ID NO:3.

In a further aspect, the present invention discloses a method for treating or preventing a hyperproliferative disorder by administering an effective amount of a compound of formula (I):

wherein:
Ar is a five or six membered unsubstituted or substituted aromatic ring that is optionally fused to an aromatic or heteroaromatic ring;
B is a bond, CO, $SO_2$ or $(CH_2)_n$ wherein n=1-5; and
$R_1$ and $R_2$ are each independently H, alkyl or aryl groups that are optionally substituted. In another embodiment of the invention, Ar of formula I is phenyl, pyridyl, napthyl, triazine, triazole, quinoxaline, dibenzofuran, benzimidazole, indene, indeno oxadiazine, indazole or an indole ring; B is a bond, CO or $(CH_2)_n$ wherein n=1; and $R_1$ and $R_2$ are both H.

In another embodiment of the invention, formula I is 3-amino-1,2,4-Triazine, 3-amino-1,2,4-triazole, 2-methyl-4-nitroaniline, 2-iodo-4-nitroaniline, 4-amino-3-chloro-5-methylbenzoic acid, 1-(4'Aminophenyl)-1,2,4-triazole, 2-acetamidophenol, 5-chloro-2,3-dihydroxypyridine, 2-methyl-3-(1H-pyrazol-5-yl)imidazo(1,2-a)pyridine, 5-nitro-2,3-dihydro-1H-benzo(d)imidazol-2-one, 4-(methylamino) pyridine, 2-Chloro-4-nitrobenzamide, 2-ethylformanilide, 6-aminoindazole, 2,3-diaminobenzoic acid, 1-(5-chloro-2-methylphenyl)-2-thiourea, 4,5-diiodo-1H-imidazole, 1H-indene-1,3(2H)-dione 1-methylhydrazone, 3-hydroxyindole, 3,4-dihydro-1H-quinoxalin-2-one, 1S,6S,7R,8R,8aR)-1,6,7,8-Tetrahydroxyoctahydroindolizidine, 2-naphthalen-1-yl-2,3-dihydro-1H-pyrimidine, benzo(b)thiophen-3-ylmethylamine, 1-allyl-2-4-dioxo-1-2-3-4-tetrahydro-5-pyrimidinecarbonitrile, Methyl(S)—N-(7-chloro-2,3,4a,5-tetrahydro-4a-(methoxycarbonyl)indeno(1,2-e)(1,3,4) oxadiazin-2-ylcarbonyl)-4'-(trifluoromethoxy)carbanilate (Indoxacarb-MP), or 4-acetylpyridine and thioisonicotinamide.

In another embodiment, formula I is 4-(aminomethyl)piperidine. Typically, the formula I compound has a molecular weight of less than about 2000 daltons; in another embodiment of the invention, and preferably, less than about 500 daltons.

In another aspect of the invention, a method is disclosed the method for treating or preventing a hyperproliferative disorder with a compound of formula (II):

wherein:
A is a 3-6 membered substituted or unsubstituted cycloaliphatic or a heterocycloaliphatic ring, each of which is optionally fused to an aromatic ring;
B is a bond, CO, $SO_2$ or $(CH_2)_n$ wherein n=1-3; and
$R_1$ and $R_2$ are each independently H, alkyl or aryl groups that are optionally substituted.

Preferably, A is a heterocycloaliphatic ring comprising, at least one nitrogen atom and optionally, one or more additional heteroatoms selected from the group consisting of: nitrogen (N), oxygen (O) and sulfur (S); B is a bond, CO or $(CH_2)_n$ wherein n=1; and $R_1$ and $R_2$ are both H. In another embodiment of the invention, the cycloaliphatic or heterocycloaliphatic ring of formula II comprise one or more substituents selected from the group consisting of hydroxyl, halogen, CO and alkyl.

In a preferred embodiment, the formula II compound is 1-phenyl-4-methyl-3-pyrazolidone, 4-(aminomethyl)piperidine, N-Phenyl-p-phenylenediamine, 5-(aminomethyl)-3-(2H)-isoxazolone (Muscimol), (R)-2-aminomethylpyrrolidine, 2-pyrrolidinone oxime and 1-cyclopropylethylamine.

Typically, the formula II compounds have a molecular weight of less than about 2000 daltons, and preferably, less than about 500 daltons.

In another aspect of the invention, a method is disclosed for treating or preventing a hyperproliferative disorder with an effective amount of the compound which is an aromatic or heteroaromatic compound comprising a piperidinyl, phenyl, quinolinyl and isoquinolinyl ring and having one or more nitrogen containing substituents selected from the group consisting of $NR_3R_4$, $(CH_2)_nNR_3R_4$, $CONH_2$, NH—NH—$R_5$ and C(S)—NH—$R_6$, wherein $R_3$, $R_4$, $R_5$ and $R_6$ are independently H, alkyl, cycloalkyl and aryl, and n is 1-5. In further embodiment of the invention, the aromatic or heteroaromatic compound is 4-methylcyclohexylamine, 3-(dimethylamino)-1-(5-fluoro-2-hydroxyphenyl)prop-2-en-1-one, 3-ethoxyphenethylamine, 4-fluorobenzenesulfonamide, 2-((4-fluorophenyl)-hydrazono)malononitrile, 3-fluoro-4-hydroxybenzaldehyde or 1-aminoisoquinoline. Typically, the aromatic or heteroaromatic compound of the invention is less than about 2000 daltons, and preferably, less than about 500 daltons.

In still another aspect of the invention, a method is disclosed the method for treating or preventing a hyperproliferative disorder with an effective amount of a compound that is a 7 or 8 membered monocyclic or bridged bicyclic compound with a cycloheptyl, cyclooctyl, and bicyclo(2,2,1) heptenyl having one or more substituents selected from the group consisting of $NR_3R_4$, $(CH_2)_nNR_3R_4$, $CONH_2$, NH—NH—$R_5$ and C(S)—NH—$R_6$, wherein $R_3$, $R_4$, $R_5$ and $R_6$ are independently H, alkyl, cycloalkyl and aryl, and n is 1-5. In a further embodiment of the invention, the 7 or 8-membered monocyclic or bridged bicyclic compound is 6,7-dihydro-5H-dibenzo(a,c)cycloheptene-6-carboxylic acid, N-bicyclo (2.2.1)hept-5-en-2-ylthiourea, or N1-cyclooctyl-4-hydroxy-1-piperidinecarbothioamide. Typically, the 7 or 8-membered monocyclic or bridged bicyclic compound has a molecular weight of less than about 2000 daltons, and preferably, less than about 500 daltons.

In a final aspect of the invention, a method is disclosed to treat or prevent a ubiquitin conjugating enzyme disorder by administering an effective amount of a composition of the invention. In one embodiment, the ubiquitin conjugating related disorder is a hyperproliferative disorders, Cystic Fibrosis, Huntington's, Alzheimer's, or Parkinson's disease.

DEFINITIONS

Figure 1:
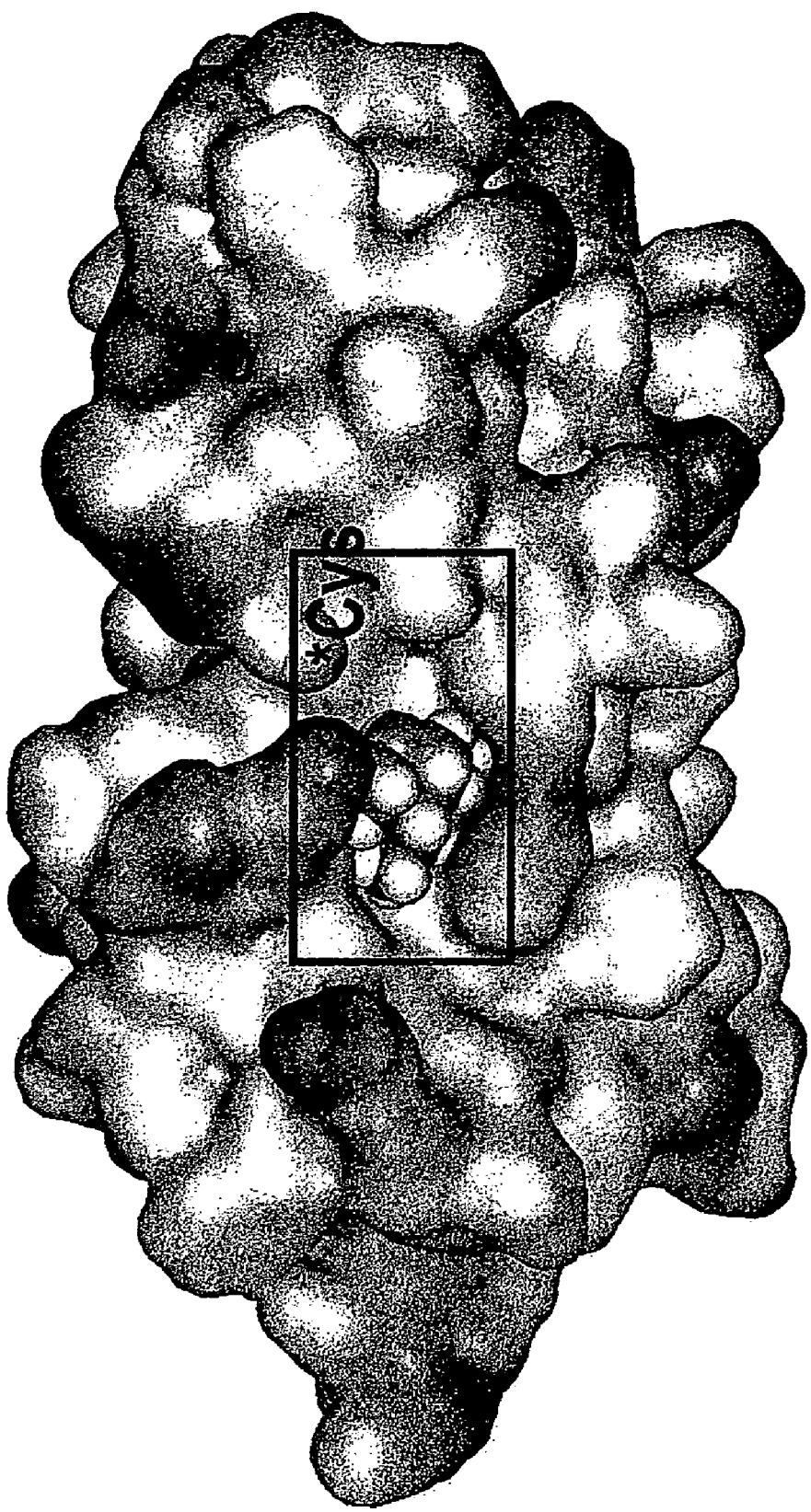
FIG. 1 shows a 3-D computer representation of Ubc4 binding HBS01.

As used herein an "ubiquitin conjugating enzyme," "Ubc" or "E2" is a family of proteins which are capable of forming a thiol ester adduct with the C-terminal carboxyl group of ubiquitin and transferring the ubiquitin to an amino group in an acceptor protein by formation of an isopeptide bond. The biological activity of "ubiquitin conjugating enzymes" can be characterized by an ability to mediate ubiquination of cellular and/or viral proteins, e.g. cell-cycle regulatory proteins such as p53, myc, fos, and cyclins. Such a feature will typically be marked by an ability of "Ubc" to mediate ubiquitin-dependent degradation or inactivation of such regulatory proteins, in normal proliferating cells, in virally-infected cells, e.g. by papillomavirus or adenovirus, or in transformed cells, e.g. in cancerous cells.

The "Ubcs" include those present in yeast and mammalian organisms such as humans, rat and mice. "Ubcs" may be selected from those available in the art by one of skill in the art. Non-limiting examples include yeast Ubc1, Ubc2, Ubc3, Ubc4, Ubc5, Ubc6, Ubc7, Ubc8, Ubc10, Ubc13, and their human, mouse and rat homologs.

A "variant" of a "Ubc" refers to a "Ubc" substantially similar to either the entire protein, or a fragment thereof. A "fragment" of a "Ubc", such as any of the "Ubc" discussed herein, is meant to refer to any "Ubc" protein or the corresponding 3-D co-ordinates of a subset of an individual "Ubc" that contains at least one "active site."

As used herein an "active site" is a region on a "Ubc" within 20 Å radius, as determined by 3-D computer modeling, of the "catalytic cysteine" or the "E1 binding consensus," that is physically and energetically favorable for binding an organic compound. The "catalytic cysteine" is located at the amino acid position corresponding to Cys86 of SEQ ID NO:1. The "E1 binding consensus" is located at the amino acid positions corresponding to Lys5, Arg6, Lys9 and Glu10 of SEQ ID NO:1. An "active site" is identified by the methods disclosed herein, preferably by a molecular topology and charge visualization technique. The "catalytic site" is a region within a 20 Å radius of the "catalytic cysteine." As used herein, the "E1 binding site" is a region within a 20 Å radius of the "E1 binding consensus."

As used herein a "binding domain" is a region within the "active site" containing one or more amino acids which bind an organic compound. Typically, the "binding domain" allows for one or more hydrogen binding interactions with the organic compound such that an energetically favorable binding event occurs. The "binding domain" may also include hydrophobic interactions. An example of a "binding domain" is the amino acid residues corresponding to Pro66, Ile85 and Leu90 of SEQ ID NO:1.

As used herein a "library of organic compounds" is a collection of data which represents the 3-D coordinates of multiple chemical organic compounds. Examples of a "library of organic compounds" include the Available Chemical Directory (MDL Inc., San Leandro, Calif.), the Derwent World Drug Index (WDI), BioByteMasterFile, and the National Cancer Institute database (NCI). A "modified library of organic compounds" is a "library of organic compounds" which have been altered to include hydrogens.

As used herein, "pharmacologically effective amount," "therapeutically effective amount" or simply "effective amount" refers to that amount of an agent effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease of disorder is the amount necessary to effect that at least 25% reduction.

As used herein, a "hyperproliferative disorder" means cancer, neoplastic growth, hyperplastic or proliferative growth or a pathological state of abnormal cellular development and includes solid tumors, non-solid tumors, and any abnormal cellular proliferation, such as that seen in leukemia. As used herein, "hyperproliferative disorder" also means angiogenesis-dependent cancers and tumors, i.e., tumors that require for their growth (expansion in volume and/or mass) an increase in the number and density of the blood vessels supplying them with blood.

As used herein, the term "homology" refers to the optimal alignment of sequences (either nucleotides or amino acids), which may be conducted by computerized implementations of algorithms. "Homology" with regard to polynucleotides, for example, may be determined by analysis with BLASTN version 2.0 using the default parameters. "Homology" with respect to polypeptides (i.e., amino acids), may be determined using a program, such as BLASTP version 2.2.2 with the default parameters, which aligns the polypeptides or fragments being compared and determines the extent of amino acid identity or similarity between them. It will be appreciated that amino acid "homology" includes conservative substitutions, i.e. those that substitute a given amino acid in a polypeptide by another amino acid of similar characteristics. Typically seen as conservative substitutions are the following replacements: replacements of an aliphatic amino acid such as Ala, Val, Leu and Ile with another aliphatic amino acid; replacement of a Ser with a Thr or vice versa; replacement of an acidic residue such as Asp or Glu with another acidic residue; replacement of a residue bearing an amide group, such as Asn or Gln, with another residue bearing an amide group; exchange of a basic residue such as Lys or Arg with another basic residue; and replacement of an aromatic residue such as Phe or Tyr with another aromatic residue.

As used herein in relation to the position of an amino acid, e.g., Cys86 of SEQ ID NO:1, the term "corresponding to" refers to an amino acid in a first polypeptide sequence that aligns with a given amino acid in a reference polypeptide sequence when the first polypeptide and reference polypeptide sequences are aligned. Alignment is performed by one of skill in the art using software designed for this purpose, for example, BLASTP version 2.2.2 with the default parameters for that version. As an example of amino acids that "correspond," Cys86 of Ubc4 of SEQ ID NO:1 "corresponds to" Cys89 of Ubc7 of SEQ ID NO:3, and vice versa.

As herein defined, the term "selectively binds" means that the interaction between the organic compound and the Ubc are specific, that is, in the event that a number of molecules are presented to the organic compound, the latter will only bind to one or a few of those molecules presented. Preferably, the compound will only target a single Ubc enzyme. Advantageously, the compound-Ubc interaction will be of high affinity. Non-covalent interactions such as hydrogen bonding and Van der Waals interactions will mediate the discriminate interaction between the compound and a specific Ubc only.

DETAILED DESCRIPTION

As described herein the present invention provides methods and compositions for selectively targeting one or more active sites of a Ubc. The invention also relates to structure based screening methods to identify organic compounds that selectively bind one or more of the Ubc's active sites with in silico techniques, thus providing an inexpensive and quick method for the identification of compounds that selectively modulate Ubcs. It is expected that modulating protein degradation via the targeting of specific Ubc active sites will treat a variety of disorders in which Ubcs have been implicated, particularly hyperproliferative disorders.

The present invention provides methods for specifically targeting Ubcs. The invention utilizes the structure based design programs (InsightII, Accelrys, Inc., San Diego, Calif.) and LUDI (Boehm, *J. Comp. Aid. Mol. Des.* 6:61-78; Accelrys, Inc., San Diego, Calif.) to identify domains within active sites that selectively bind chemical compounds and interfere with Ubc function. InsightII is used to recognize molecular topology and electrostatic charges in specific active sites in the Ubcs that are physically and energetically favorable to bind a compound in an organic compound library, while LUDI (Accelrys, Inc., San Diego, Calif.) is used to analyze and score binding between a compound in an organic compound library and the active site identified by InsightII. The structure based design methods of the present invention have identified efficacious compounds, e.g., HBS01, for the treatment of Ubc disorders, e.g., cancer.

These compounds of the invention specifically target the Ubc catalytic site and E1 binding sites. Many of these compounds have been tested in vivo and in vitro and have proved to selectively target Ubcs and inhibit cellular proliferation in cancer models. A compound designated HBS01, which is 4-(aminomethyl)piperidine, was identified by the in silico screening techniques described herein. In vitro testing revealed HBS01 was a potent cytotoxic agent with an IC50 of 30 nm against the human colon cancer cell line C85 (Longo et al. Oncol. Res., 12(8):309-14), and the breast cancer cell lines MCF-7 and MCF-7Adr. HBS01 inhibited the growth of established tumors in nude mice and delayed tumor growth in mice pretreated with HBS01. These studies also revealed that the HBS01 agent is well tolerated with a maximum tolerated dose in mice of 1.4 g/kg, whereas the therapeutic dose being only 17 mg/kg.

Ubcs of the Invention

There are 42 human Ubcs and 13 yeast Ubcs that have been identified to date. The Ubc protein family is structurally well characterized. The E2 core domain consists of: four standard α helices, a $3_{10}$ helix and four to seven stranded antiparallel β sheets. The catalytic cysteine lies in a long loop that connects the β sheet and α2 helix. This catalytic cysteine is located at the amino acid position corresponding to Cys86 of SEQ ID NO:1. SEQ ID NO:1 shows the amino acid sequence of *S. cerevisiae* Ubc4 (Accession No. P15731), SEQ ID NO:2 shows the amino acid sequence of human Ubc5a (Accession No. P51668) and SEQ ID NO:3 shows the amino acid sequence of *S. cerevisiae* Ubc7 (Accession No. S28951). In some Ubcs like Ubc 7 and CDC34 (Ubc3), a long and flexible loop is present near the catalytic site. Some E2 enzymes have C and N terminal extensions and which have been shown to be catalytically important. The presence or absence of these extensions can be used to classify the E2s into 4 classes: Class I Ubcs consist of a highly conserved core catalytic domain and share 25% identity between members; class II Ubc enzymes have an additional C terminal extension; class III Ubcs have an additional N terminal extension; and class IV Ubcs have both C and N terminal extensions.

Any known or unknown Ubc can be used in the methods described herein by one of ordinary skill in the art. Additionally, Ubcs can be identified based on sequence alignments of sequences described herein. For example, Ubcs can be identified based on sequence alignments of sequences which include amino acid residues corresponding to Gly49, Tyr61, Pro62, Pro66, His76 to Asn78, Gly83, Cys86, Leu87, Trp94 and Pro96 of SEQ ID NO:1. Non-limiting examples of Ubcs include yeast Ubc1, Ubc2, Ubc3, Ubc4, Ubc5, Ubc6, Ubc7, Ubc8, Ubc10, Ubc13, and their human, mouse and rat homologs. In some embodiments, the Ubcs are mammalian human Ubcs. In other embodiments the Ubcs are yeast Ubcs. In a preferred embodiment the Ubc is yeast Ubc4 of SEQ ID NO:1. Additional, Ubcs that may be utilized in the present invention include: Ubiquitin-conjugating enzyme E2 4 (*S. cerevisiae*) (Accession No. P15731), Ubiquitin-conjugating enzyme E2-17 kDa 2 (*Homo sapiens*) (Accession No. P51669), ubiquitin-conjugating enzyme E2D 3 (*Homo sapiens*) (Accession No. Q9Y2.times.8), Ubiquitin-conjugating enzyme E2-18 kDa UbCH7 (*Homo sapiens*) (Accession No. P51966), Ubiquitin-conjugating enzyme E2-18 kDa (*S. cerevisiae*) (Accession No. P23567), Ubiquitin-conjugating enzyme E2-20 kDa (*S. cerevisiae*) (Accession No. P06104), Ubiquitin-conjugating enzyme E2-21.2 kDa (*S. cerevisiae*; Accession No. P52491), Ubiquitin-conjugating enzyme E2-18 kDa (*S. cerevisiae*, Accession No. P50623), Ubiquitin-conjugating enzyme E2-24 kDa (*S. cerevisiae*, Accession No. P21734), Ubiquitin-conjugating enzyme E2 13 (*S. cerevisiae*, Accession No. P52490), UbcSa (*H. sapiens*) (Accession No. P51668) and variants thereof. The amino acid sequences can be accessed at the NCBI's protein data base (having a URL address of www.ncbi.nlm.nih.gov/entrez). Additional, Ubc Accession Nos. can be accessed at a the URL address of www.ubiquitin-resource.org (login: ubq2e1, password: sentrinE2).

Ubc 3-D Co-Ordinates

The invention involves the inputting of 3-D co-ordinates of Ubcs into an electronic storage medium. In one embodiment, the complete 3-D co-ordinates of the Ubc are input. In an alternative embodiment, a fragment, or less than the complete 3-D co-ordinates are inputted. Preferably the 3-D co-ordinates at least those of the catalytic site and/or the E1 binding site. The 3-D co-ordinates may be known in the art or based on homology modeling. Known Ubc 3-D co-ordinates include Ubc2 (PDB ID No. 1AYZ), Ubc9 (PDB ID No. 1A3S), Ubc4 (PDB ID No. 1QCQ), Ubc7 (PDB ID No. 2UCZ), UbcH10 (PDB ID No. 117K) and Ubc13 (PDB ID No. 1JBB, 1J7D, 1JAT) as well as others known in the art. 3-D co-ordinates for many known Ubc can be obtained from the Protein Data Bank ("PDB") (Research Collaboratory for Structural Bioinformatics; at the URL address of www.rcsb.org or at the URL address of: www.ubiquitin-resource.org—Free Public Access. In one preferred embodiment, the 3-D co-ordinates are PDB ID No. 1QCQ. Variants of the 3-D-coordinates can also be used in the invention, such as variants in which the r.m.s. deviation of the x, y and z co-ordinates for all heavy (i.e., not hydrogen) atoms are less than 2.5 Å. In some preferred embodiments the 3-D co-ordinates are based on homology modeling with known ubiquitin 3-D co-ordinates as described herein.

The 3-D coordinates are used to generate a 3-D structural model (or a representation thereof) for performing the method of the invention. Preferably, the 3-D coordinates may be used to generate a computer model for the structure. The 3-D coordinates comprising the Ubcs is built from all or a fraction of the 3-D coordinates of the Ubcs. Thus, for example, the 3-D co-ordinates provided in the 3-D structure and/or model structure may comprise the amino acid residues of the Ubcs, or a portion of the Ubcs or a homologue thereof useful in the modeling and design of test compounds capable of binding to domains within active sites.

Homology modeling (also known as comparative modeling or knowledge-based modeling) methods develop a three dimensional model from a polypeptide sequence based on the structures of known proteins (e.g., native or mutated Ubcs). In the present invention the method utilizes a computer representation of a Ubc structure or a complex of same, a computer representation of the amino acid sequence of a polypeptide with an unknown structure (additional native or mutated Ubc), and standard computer representations of the structures of amino acids. In particular, the method comprises the steps of: (a) identifying structurally conserved and variable regions in the known structure; (b) aligning the amino acid sequences of the known structure and unknown structure (c) generating coordinates of main chain atoms and side chain atoms in structurally conserved and variable regions of the unknown structure based on the coordinates of the known structure thereby obtaining a homology model and (d) refining the homology model to obtain a three dimensional structural model for the unknown structure. Similar methods are known to those skilled in the art (Greer, 1985, Science 228, 1055; Bundell et al 1988, Eur. J. Biochem. 172, 513; Knighton et al., 1992, Science 258:130-135, the URL address of biochem.vt.edu/courses/modeling/homology.htm). Computer programs that can be used in homology modeling include Quanta and the homology module in the Insight II modeling package (Accelrys, Inc., San Diego, Calif.) or MODELLER (Rockefeller University, the URL address of www.iucr.ac:uk/sinristop/logical/prg-modeller.html, Sali's Modeller also from Accelrys, Inc., San Diego, Calif.).

In step (a) of the homology modeling method, the known Ubc structure is examined to identify the structurally conserved regions (SCRs) from which an average structure, or framework, can be constructed for these regions of the protein variable regions (VRs), in which known structures may differ in conformation, also must be identified. SCRs generally correspond to the elements of secondary structure, such as alpha-helices and beta-sheets, and to ligand and substrate-binding sites (e.g., acceptor and donor binding sites). The VRs usually lie on the surface of the proteins and form the loops where the main chain turns. Many methods are available for sequence alignment of known structures and unknown structures. Sequence alignments generally are based on the dynamic programming algorithm of Needleman and Wunsch (J. Mol. Biol. 48: 442-453, 1970). Current methods include FASTA, Smith-Waterman, and BLASTP, with the BLASTP method differing from the other two in not allowing gaps. Scoring of alignments typically involves construction of a 20×20 matrix in which identical amino acids and those of similar character (i.e., conservative substitutions) may be scored higher than those of different character. Substitution schemes which may be used to score alignments include the scoring matrices PAM (Dayhoff et al., Meth Enzymol. 91: 524-545, 1983), and BLOSUM (Henikoff and Henikoff, Proc. Nat. Acad. Sci. USA 89: 10915-1'0919, 1992), and the matrices based on alignments derived from three-dimensional structures including that of Johnson and Overington (JO matrices) (J. Mol. Biol. 233: 716-738, 1993). Other methods of determining sequence alignment are described herein.

Alignment based solely on sequence may be used; however, other structural features also may be taken into account. In Quanta, multiple sequence alignment algorithms are available that may be used when aligning a sequence of the unknown with the known structures. Four scoring systems (i.e., sequence homology, secondary structure homology, residue accessibility homology; CA-CA distance homology) are available, each of which may be evaluated during an alignment so that relative statistical weights may be assigned.

When generating coordinates for the unknown structure, main chain atoms and side chain atoms, both in SCRs and VRs need to be modeled. A variety of approaches known to those skilled in the art may be used to assign coordinates to the unknown. In particular, the coordinates of the main chain atoms of SCRs will be transferred to the unknown structure. VRs correspond most often to the loops on the surface of the polypeptide and if a loop in the known structure is a good model for the unknown, then the main chain coordinates of the known structure may be copied. Side chain coordinates of SCRs and VRs are copied if the residue type in the unknown is identical to or very similar to that in the known structure. For other side chain coordinates, a side chain rotamer library may be used to define the side chain coordinates. When a good model for a loop cannot be found fragment databases may be searched for loops in other proteins that may provide a suitable model for the unknown. If desired, the loop may then be subjected to conformational searching to identify low energy conformers.

Once a homology model has been generated it is analyzed to determine its correctness. A computer program available to assist in this analysis is the Protein Health module in Quanta which provides a variety of tests. Other programs that provide structure analysis along with output include PROCHECK and 3-D-Profiler (Luthy R. et al, Nature 356: 83-85, 1992; and Bowie, J. U. et al, Science 253: 164-170, 1991). Once any irregularities have been resolved, the entire structure may be further refined. Refinement may consist of energy minimization with restraints, especially for the SCRS. Restraints may be gradually removed for subsequent minimizations. Molecular dynamics may also be applied in conjunction with energy minimization.

Storage Medium

The storage medium in which the 3-D co-ordinates are provided is preferably random-access memory (RAM), but may also be read only memory (ROM e.g. CDROM), or a diskette. The storage medium may be local to the computer, or may be remote (e.g., a networked storage medium, including the internet). Any suitable computer can be used in the present invention.

Active Site Determination

Active sites can be determined from the 3-D coordinates of the Ubcs utilizing the present invention. Molecular modeling techniques can be applied to the 3-D coordinates of at least a fragment of an Ubc to derive 3-D models and identify active sites within the Ubc catalytic and E1 binding sites. In a preferred embodiment, the active sites are within a 20 Å radius of the amino acid corresponding to Cys86 of SEQ ID NO:1 as determined in a 3-D model. In another preferred embodiment, the active sites are within a 20 Å radius of the putative E1 binding site which includes the amino acids corresponding to Lys5, Arg6, Lys9 and Glu10 of SEQ ID NO:1.

The molecular modeling techniques identify Van der Waals contacts, electrostatic interactions, and/or hydrogen bonding opportunities. InsightII (Accelrys, Inc., San Diego, Calif.) is used to recognize molecular topology and electrostatic charges in specific active sites in the Ubcs and/or multiple copy simultaneous search (MCSS) techniques which map favorable interaction positions for functional groups. The InsightII program identifies contours for the various functional probes which identify the shape of the pocket and energetically favorable active sites. This preferably reveals positions in the Ubcs for interactions such as, but not limited to, those with protons, hydroxyl groups, amine groups, hydrophobic groups (e.g., methyl, ethyl, benzyl) and/or divalent cations. In a preferred embodiment, the active sites are determined using the InsightII (Accelrys, Inc., San Diego, Calif.) program.

Identification of Compounds that Bind to Ubc Active Sites

Once the specific active sites have been identified an in silico binding interaction is performed between the active sites and a library of organic compounds. In a preferred embodiment, the library of organic compounds is a digital library. The binding interaction is performed with a database searching program which is capable of scanning a database of small molecules of known three-dimensional structure for candidates which fit into the active site. Suitable software programs include CATALYST (Molecular Simulations Inc., San Diego, Calif.), UNITY (Tripos Inc., St Louis, Mo.), FLEXX (Rarey et al., *J. Mol. Biol.* 261: 470-489 (1996)), CHEM-3-DBS (Oxford Molecular Group, Oxford, UK), DOCK (Kuntz et al., *J. Mol. Biol.* 161: 269-288 (1982)), and MACCS-3-D (MDL Information Systems Inc., San Leandro, Calif.) and LUDI (Boehm, *J. Comp. Aid. Mol. Des.* 6:61-78 (1992)), CAVEAT (Bartlett et al. in "Molecular Recognition in Chemical and Biological Problems", special publication of *The Royal Chem. Soc.*, 78:182-196 (1989)) and MCSS (Miranker et al. *Proteins* 11: 29-34 (1991)). Prior to performing the binding interaction it is preferable to add hydrogens to the library of organic compounds. Those of ordinary skill in the art will understand that hydrogens can be added to structures by most molecular graphics software, including Insight II (InsightII, Accelrys, Inc., San Diego, Calif.). Relevant binding domains are identified using the software by: (1) identifying chemical groups on amino acids within the active site that allow for binding interactions, thus identifying possible interaction sites; (2) screening a library of organic compounds that interact with one or more interaction sites in the active sites, thus identifying a binding domain; and (3) scoring the Ubc-organic compound complex. In one preferred embodiment, the library of organic compounds has been modified to contain hydrogen atoms. In another preferred embodiment, the binding interaction is performed with the LUDI program (Boehm, 1992).

A set of interaction sites are generated for each chemical group or functional groups of a Ubc. This set of interaction sites encompasses the range of suitable positions for a ligand atom or functional group involved in the putative interaction. There are four classes of interaction sites which include: H bond-donor; H bond-acceptor; Lipophilic-aliphatic; and Lipophilic-aromatic. The H bond-donor and H bond-acceptor interaction sites are suitable sites for hydrogen bond formation. The aliphatic and aromatic interaction sites are suitable sites for hydrophobic interactions. The interaction sites are then analyzed for van der Waals interactions with the Ubc. The organic compounds are then fitted into the interaction sites by RMS superposition of the atoms by the software program, thus identifying binding sites with the organic compound. A method of using LUDI to search for chemicals which bind 3-D protein structures is taught in Boehm. *Journal of Computer-Aided Molecular Design*, 8:623-632 (1994), which is herein incorporated by reference.

Suitable libraries of organic compounds for use in the invention include the Available Chemicals Directory (MDL Inc), the Derwent World Drug Index (WDI), BioByteMaster-File, the National Cancer Institute database (NCI), and the Maybridge catalog, Aldrige/Sigma Rare Chemicals library as well as others known in the art. In a preferred embodiment, the library of organic compounds is the Available Chemical Directory. After binding events occur the results are scored based on a scoring function which indicates binding affinity and formation of hydrogen bonds and ionic interactions. In one embodiment the scoring function is the Boehm scoring function as described in Boehm. *Journal of Computer-Aided Molecular Design*, 12:309-323 (1998), which is herein incorporated by reference. The highest scored compounds are then manually selected to eliminate compounds which excessively protrude out of the binding site, as visualized by the computer 3-D structure of the Ubc and organic compound. The compounds remaining can then be tested in vitro and in vivo as described herein.

Compounds Identified by the Method of the Invention

The selective ubiquitin conjugating enzyme inhibitor compounds of the invention function by binding selectively to the catalytic domain or the E1 binding site present in the Ubc. Without wishing to be bound by theory, such selective binding is accomplished by phobic-phobic interactions between the hydrogen atoms present in the inhibitor compounds and hydrophobic domains on the enzyme, which is facilitated by the optimal size and conformation of the inhibitor compounds of the invention with respect to enzyme hydrophobic domains. Compounds of the invention are known by those of ordinary skill in the art. The compounds of the invention can be obtained from commercial suppliers including: Sigma-Aldrich (St. Louis, Mo.), Maybridge (Cornwall, England), Acros Organics (Morris Plains, N.J.), Oakwood Products, Inc. (West Columbia, S.C.), Specs (Wakefield R.I.), Combi-Blocks, Inc (San Diego, Calif.), and CombiChem.net (Sudbury, UK).

In one embodiment of the present invention, the ubiquitin conjugating enzyme inhibitor compounds that selectively bind to the enzyme catalytic site are described by formula (I):

$$\text{Ar—B—NR}_1\text{R}_2 \qquad (I)$$

wherein:
Ar is a five or six membered unsubstituted or substituted aromatic ring that is optionally fused to an aromatic or heteroaromatic ring;
B is a bond, CO, $SO_2$ or $(CH_2)_n$ wherein n=1-5; and
$R_1$ and $R_2$ are each independently H, alkyl or aryl groups that are optionally substituted.

Preferred compounds of formula I include, but are not limited to compounds in which Ar comprises a phenyl, pyridyl, napthyl, triazine, triazole, quinoxaline, dibenzofuran, benzimidazole, indene, indeno oxadiazine, indazole or an indole ring; B is a bond, CO or $(CH_2)_n$ wherein n=1; and $R_1$ and $R_2$ are both H.

Currently preferred compounds of formula (I) include:
3-amino-1,2,4-Triazine;
3-amino-1,2,4-Triazole;
2-methyl-4-nitroaniline;
2-iodo-4-nitroaniline;
4-amino-3-chloro-5-methylbenzoic acid;
1-(4'Aminophenyl)-1,2,4-triazole;
2-acetamidophenol;
5-chloro-2,3-dihydroxypyridine;
2-methyl-3-(1H-pyrazol-5-yl)imidazo(1,2-a)pyridine;
5-nitro-2,3-dihydro-1H-benzo(d)imidazol-2-one;
4-(methylamino)pyridine;
2-chloro-4-nitrobenzamide;
2-ethylformanilide;
6-aminoindazole;
2,3-diaminobenzoic acid;
1-(5-chloro-2-methylphenyl)-2-thiourea;
4,5-diiodo-1H-imidazole;
1H-indene-1,3(2H)-dione 1-methylhydrazone;
3-hydroxyindole;
3,4-dihydro-1H-quinoxalin-2-one;
1S,6S,7R,8R,8aR)-1,6,7,8-Tetrahydroxyoctahydroindolizidine;
2-naphthalen-1-yl-2,3-dihydro-1H-pyrimidine;
benzo(b)thiophen-3-ylmethylamine;
1-allyl-2-4-dioxo-1-2-3-4-tetrahydro-5-pyrimidinecarbonitrile; Methyl(S)—N-(7-chloro-2,3,4a,5-tetrahydro-4a-(methoxycarbonyl)indeno(1,2-e)(1,3,4)oxadiazin-2-yl-carbonyl)-4'(trifluoromethoxy)carbanilate (Indoxacarb-MP);
4-acetylpyridine; and
thioisonicotinamide.

In another embodiment of the present invention, the ubiquitin conjugating enzyme inhibitor compounds that selectively bind to the enzyme catalytic site are described by formula (II):

A-(B—NR$_1$R$_2$)    (II)

wherein:
A is a 3-6 membered substituted or unsubstituted cycloaliphatic or heterocycloaliphatic ring that is optionally fused to an aromatic ring;
B is a bond, CO, SO$_2$ or $(CH_2)_n$ wherein n=1-3; and
$R_1$ and $R_2$ are each independently H, alkyl or aryl groups that are optionally substituted.

Preferred compounds of formula II include, but are not limited to compounds in which the heterocycloaliphatic ring comprises at least one nitrogen atom and optionally, additional heteroatoms including nitrogen (N), oxygen (O) and sulfur (S); B is a bond, CO or $(CH_2)_n$ wherein n=1; and $R_1$ and $R_2$ are both H. Preferred ring substituents in the cycloaliphatic or heterocycloaliphatic ring in compounds of formula II include one or more atoms or groups chosen from hyroxyl, halogen, CO and alkyl.

Currently preferred compounds of formula (II) include:
1-Phenyl-4-methyl-3-pyrazolidone;
4-(Aminomethyl)piperidine;
N-Phenyl-p-phenylenediamine;
5-(aminomethyl)-3-(2H)-isoxazolone (Muscimol);
(R)-2-aminomethylpyrrolidine;
2-pyrrolidinone oxime; and
1-cyclopropylethylamine.

In another embodiment of the present invention, the ubiquitin conjugating enzyme inhibitor compounds that selectively bind to the E1 binding site in the enzyme are substituted or unsubstituted cycloaliphatic or aromatic ring compounds preferably containing one or more nitrogen atoms in the ring, in one or more of the substituents groups, or both.

Preferred enzyme E1 binding site compounds of the invention comprise monocyclic and bridged 7 or 8-membered carbocyclic rings, including cycloheptyl, cyclooctyl and bicyclo (2,2,1) heptenyl rings; piperidinyl; phenyl; quinolinyl and isoquinolinyl rings. Preferred nitrogen containing substitutents included NR$_3$R$_4$, $(CH_2)_n$NR$_3$R$_4$, CONH$_2$, NH—NH—R$_5$ and C(S)—NH—R$_6$, wherein R$_3$, R$_4$, R$_5$ and R$_6$ are independently H, alkyl, cycloalkyl and aryl, and n is 1-5.

Currently preferred ubiquitin conjugating enzyme E1 binding site compounds of the invention include:
N-1-cyclooctyl-4-hydroxy-1-piperidinecarbothioamide;
6,7-dihydro-5H-dibenzo(a,c)cycloheptene-6-carboxylic acid;
4-Methylcyclohexylamine;
3-(dimethylamino)-1-(5-fluoro-2-hydroxyphenyl)prop-2-en-1-one;
3-Ethoxyphenethylamine;
N-bicyclo(2.2.1)hept-5-en-2-ylthiourea;
4-Fluorobenzenesulfonamide;
2-((4-fluorophenyl)hydrazono)malononitrile;
3-Fluoro-4-hydroxybenzaldehyde; and
1-Aminoisoquinoline.

In Vitro and In Vivo Testing of the Identified Compounds

The compounds of the invention may be demonstrated to inhibit tumor cell proliferation, cell transformation and tumorigenesis in vitro or in vivo using a variety of assays known in the art, or described herein. Such assays can use cells of a cancer cell line or cells from a patient. Many assays well-known in the art can be used to assess such survival and/or growth, for example, cell proliferation can be assayed by measuring (3H) thymidine incorporation, by direct cell count, by detecting changes in transcription, translation or activity of known genes such as proto-oncogenes (e.g., fos, Myc) or cell cycle markers (Rb, cdc2, cyclin A, cyclin B, D1, D2, or E). The levels of such protein and mRNA and activity can be determined by any method well known in the art. For example, protein can be quantitated by known immunodiagnostic methods such as Western blotting or immunoprecipitation using commercially available antibodies (for example, many cell cycle marker antibodies can be obtained from Santa Cruz, Inc.). mRNA can be quantitated by methods that are well known and routine in the art, for example by Northern analysis, RNase protection, the polymerase chain reaction in conjunction with reverse transcription, etc. Cell viability can be assessed by using trypan-blue staining or other cell death or viability markers known in the art. Differentiation can be assessed visually based on changes in morphology, etc. The present invention provides for cell cycle and cell proliferation analysis by a variety of techniques known in the art, including but not limited to the following those disclosed herein. As one example, bromodeoxyuridine ("BRDU") incorporation may be used as an assay to identify proliferating cells. The BRDU assay identifies a cell population undergoing DNA synthesis by incorporation of BRDU into newly synthesized DNA. Newly synthesized DNA may then be detected using an anti-BRDU antibody (see Hoshino 30 et al., 1986, Int. J. Cancer 38, 369; Carnpana et al., 1988, J. Imunol. Moth. 107, 79).

Cell proliferation may also be examined using (3H)-thymidine incorporation (see, e.g., Chen, J., 1996, Oncogene 13:1395-403; Jeoung, J., 1995, J. Biol. Chem. 270:18367 73).

This assay allows for quantitative characterization of S-phase DNA synthesis. In this assay, cells synthesizing DNA will incorporate (3H)-thymidine into newly synthesized DNA. Incorporation may then be measured by standard techniques in the art such as by counting of radioisotope in a Scintillation counter (e.g., Beckman LS 3800 Liquid Scintillation Counter).

Detection of proliferating cell nuclear antigen (PCNA) may also be used to measure cell proliferation. PCNA is a 36 kilodalton protein whose expression is elevated in proliferating cells, particularly in early G1 and S phases of the cell cycle and therefore may serve as a marker for proliferating cells. Positive cells are identified by immunostaining using an anti-PCNA antibody (see Li et al., 1996, Curr. Biol. 6:189-199; Vassilev et al., 10 1995, J. Cell Sci. 108:1205-15).

Cell proliferation may be measured by counting samples of a cell population over time (e.g., daily cell counts). Cells may be counted using a hemacytometer and light microscopy (e.g., HyLite hemacytometer, Hausser Scientific). Cell number may be plotted against time in order to obtain a growth curve for the population of interest. In a preferred embodiment, cells counted by this method are first mixed with the dye Trypan-blue (Sigma), such that living cells exclude the dye, and are counted as viable members of the population. DNA content and/or mitotic index of the cells may be measured, for example, based on the DNA ploidy value of the cell. For example, cells in the G1 phase of the cell cycle generally contain a 2N DNA ploidy value. Cells in which DNA has been replicated but have not progressed through mitosis (e.g., cells in S-phase) will exhibit a ploidy value higher than 2N and up to 4N DNA content. Ploidy value and cell-cycle kinetics may be further measured using propidum iodide assay (see, e.g., Turner, T., et al., 1998, Prostate 34:175-81). Alternatively, the DNA ploidy may be determined by quantitation of DNA Feulgen staining (which binds to DNA in a stoichiometric manner) on a computerized microdensitometry staining system (see, e.g., Bacus, S., 1989, Am. J. Pathol. 135:783-92).

In an another embodiment, DNA content may be analyzed by preparation of a chromosomal spread (Zabalou, S., 1994, Hereditas. 120:127-40; Pardue, 1994, Meth. Cell Biol. 44:333 351). The expression of cell-cycle proteins (e.g., CycA. CycB, CycE, CycD, cdc2, Cdk4/6, Rb, p21 or p27) provide crucial information relating to the proliferative state of a cell or population of cells. For example, identification in an anti-proliferation signaling pathway may be indicated by the induction of p21 cip 1. Increased levels of p21 expression in cells results in delayed entry into G1 of the cell cycle (Harper et al., 1993, Cell 75:805 to 816; Li et al., 1996, Curr. Biol. 6:189-199). p21 induction may be identified by immunostaining using a specific anti-p21 antibody available commercially (e.g. from Santa Cruz, Inc.). Similarly, cell-cycle proteins may be examined by Western blot analysis using commercially available antibodies. In another embodiment, cell populations are synchronized prior to detection of a cell cycle protein. Cell-cycle proteins may also be detected by FACS (fluorescence-activated cell sorter) analysis using antibodies against the protein of interest.

Detection of changes in length of the cell cycle or speed of cell cycle may also be used to measure inhibition of cell proliferation by a Organic compound. In one embodiment the length of the cell cycle is determined by the doubling time of a population of cells (e.g., using cells contacted or not contacted with one or more compounds of the invention). In another embodiment, FACS analysis is used to analyze the phase of cell cycle progression, or purify G1, S. and G2/M fractions (see, e.g., Delia, D. et al., 1997, Oncogene 14:2137-47).

Lapse of cell cycle checkpoint(s), and/or induction of cell cycle checkpoint(s), may be examined by the methods described herein, or by any method known in the art. Without limitation, a cell cycle checkpoint is a mechanism which ensures that a certain cellular events occur in a particular order. Checkpoint genes are defined by mutations that allow late events to occur without prior completion of an early event (Weiner, T., and Hartwell, L., 1993, Genetics, 134:63-80). Induction or inhibition of cell cycle checkpoint genes may be assayed, for example, by Western blot analysis, or by immunostaining, etc. Lapse of cell cycle checkpoints may be further assessed by the progression of a cell through the checkpoint without prior occurrence of specific events (e.g. progression into mitosis without complete replication of the genomic DNA).

Activity of signaling and cell cycle proteins and/or protein complexes is often mediated by a kinase activity. The present invention provides for analysis of kinase activity by assays such as the histone HI assay (see, e.g., Delia, D. et al., 1997, Oncogene 14:2137 47). The compounds of the invention can also be demonstrated to alter cell proliferation in cultured cells in vitro using methods which are well known in the art. Specific examples of cell culture models include, but are not limited to, for lung cancer, primary rat lung tumor cells (Swafford et al., 1997, Mol. Cell. Biol., 17:1366-1374) and large-cell undifferentiated cancer cell lines (Mabry et al., 1991, Cancer Cells, 3:53-58); colorectal cell lines for colon cancer (Park and Gazdar, 1996, J. Cell Biochem. Suppl. 24:131-141); multiple established cell lines for breast cancer (Hambly et al., 1997, Breast Cancer Res. Treat. 43:247-258; Gierthy et al., 1997, Chemosphere 34:1495-1505; Prasad and Church, 1997, Biochem. Biophys. Res. Commun. 232:14-19); a number of well-characterized cell models for prostate cancer (Webber et al., 1996, Prostate, Part 1, 29:386-394; Part 2, 30:58-64; and Part 3, 30:136-142; Boulikas, 1997, Anticancer Res. 17:1471-1505); for genitourinary cancers, continuous human bladder cancer cell lines (Ribeiro et al., 1997, Int. J. Radial. Biol. 72:11-20); organ cultures of transitional cell carcinomas (Booth et al., 1997, Lab Invest. 76:843-857) and rat progression models (Vet et al., 1997, Biochim. Biophys Acta 1360:39-44); and established cell lines for leukemias and lymphomas (Drexler, 1994, Leuk. Res. 18:919-927, Tohyama, 1997, Int. J. Hematol. 65:309-317).

The compounds of the invention can also be demonstrated to inhibit cell transformation (or progression to malignant phenotype) in vitro. In this embodiment, cells with a transformed cell phenotype are contacted with one or more compounds of the invention, and examined for change in characteristics associated with a transformed phenotype (a set of in vitro characteristics associated with a tumorigenic ability in vivo), for example, but not limited to, colony formation in soft agar, a more rounded cell morphology, looser substratum attachment, loss of contact inhibition, loss of anchorage dependence, release of proteases such as plasminogen activator, increased sugar transport, decreased serum requirement, or expression of fetal antigens, etc. (see Luria et al., 1978, General 30 Virology, 3-D Ed., John Wiley & Sons, New York, pp. 436-446). Loss of invasiveness or decreased adhesion may also be used to demonstrate the anti-cancer effects of the compounds of the invention. For example, a critical aspect of the formation of a metastatic cancer is the ability of a precancerous or cancerous cell to detach from primary site of disease and establish a novel colony of growth at a secondary site. The ability of a cell to invade peripheral sites is reflective of a potential for a cancerous state.

Loss of invasiveness may be measured by a variety of techniques known in the art including, for example, induction of E-cadherin-mediated cell-cell adhesion. Such E cadherin-mediated adhesion can result in phenotypic reversion and loss of invasiveness (Hordijk et al., 1997, Science 278:1464-66). Loss of invasiveness may further be examined by inhibition of cell migration. A variety of 2-dimensional and 3-dimensional cellular matrices are commercially available (Calbiochem-Novabiochem Corp. San Diego, Calif.). Cell migration across or into a matrix may be examined by microscopy, time-lapsed photography or videography, or by any method in the art allowing measurement of cellular migration. In a related embodiment, loss of invasiveness is examined by response to hepatocyte growth factor (HGF). HGF induced cell scattering is correlated with invasiveness of cells such as Madin-Darby canine kidney (MDCK) cells. This assay identifies a cell population that has lost cell scattering activity in response to HGF (Hordijk et al., 1997, Science 278:1464-66).

Alternatively, loss of invasiveness may be measured by cell migration through a chemotaxis chamber (Neuroprobe/Precision Biochemicals Inc. Vancouver, BC). In such assay, a chemo-attractant agent is incubated on one side of the chamber (e.g., the bottom chamber) and cells are plated on a filter separating the opposite side (e.g., the top chamber). In order for cells to pass from the top chamber to the bottom chamber, the cells must actively migrate through small pores in the filter. Checkerboard analysis of the number of cells that have migrated may then be correlated with invasiveness (see, e.g., Ohnishi, T., 1993, Biochem. Biophys. Res. Commun. 193: 518-25).

The compounds of the invention can also be demonstrated to inhibit tumor formation in vivo. A vast number of animal models of hyperproliferative disorders, including tumorigenesis and metastatic spread, are known in the art and are disclosed herein (see Chapter 317, "Principals of Neoplasia," in Harrison's: Principals of Internal Medicine, 13th Edition, Isselbacher et al., eds., McGraw-Hill, New York, p. 1814, and Lovejoy et al., 1997, J. Pathol. 181:130-135). Specific examples include for lung cancer, transplantation of tumor nodules into rats (Wang et al., 1997, Ann. Thorac. Surg. 64:216-219) or establishment of lung cancer metastases in SCID mice depleted of NK cells (Yono and Sone, 1997, Gan To Kagaku Ryoho 24:489-494); for colon cancer, colon cancer transplantation of human colon cancer cells into nude mice (Gutman and Fidler, 1995, World J. Surg. 19:226-234), the cotton top tamarin model of human ulcerative colitis (Warren, 1996, Aliment. Pharmacol. Ther. Supp 12:45-47) and mouse models with mutations of the adenomatous polyposis tumor suppressor (Polakis, 1997, Biochim. Biophys. Acta 1332:F127-F147); for breast cancer, kansgenic models of breast cancer (Dankort and Muller, 1996, Cancer Treat. Res. 83:71-88; Amundadittir et al., 1996, Breast Cancer Res. Treat. 39:119-135) and chemical induction of tumors in rats (Russo and Russo, 5 1996, Breast Cancer Res. Treat. 39:7-20); for prostate cancer, chemically-induced and transgenic rodent models, and human xenograft models (Royal et al., 1996, Semin. Oncol. 23:35-40), for genitourinary cancers, induced bladder neoplasm in rats and mice (Oyasu, 1995, Food Chem. Toxicol 33:747-755) and xenografts of human transitional cell carcinomas into nude rats (Jarrett et al., 1995, J. Endourol. 9:1-7); and for hematopoietic cancers, transplanted allogeneic marrow in animals (Appelbaum, 1997, Leukemia 11 (Suppl. 4):S15-S17). Further, general animal models applicable to many types of cancer have been described, including, but not restricted to, the p53-deficient mouse model (Donehower, 1996, Semin. Cancer Biol. 7:269-278), the Min mouse (Shoemaker et al., 1997, Biochem. Biophys. Acta, 1332:F25-F48), and immune responses to tumors in rat 15 (Frey, 1997, Methods, 12:173-188).

For example, a organic compound can be administered to a test animal, in one embodiment a test animal predisposed to develop a type of tumor, and the test animal subsequently examined for an decreased incidence of tumor formation in comparison with an animal not administered the Organic compound. Alternatively, a Organic compound can be administered to test animals having tumors (e.g., animals in which tumors have been induced by introduction of malignant, neoplastic, or transformed cells, or by administration of a carcinogen) and subsequently examining the tumors in the test animals for tumor regression in comparison to animals not administered the Organic compound.

Modes of Administration

The organic compounds are advantageously useful in veterinary and human medicine. For example, the compounds of the invention are useful for the treatment or prevention of hyperproliferative disorders such as cancer and neoplastic disorders. The compounds are also useful for the treatment or prevention of cystic fibrosis, neurodegenerative disorders and viral disorders.

The present pharmaceutical compositions, which comprise an effective amount of an organic compound, can be administered by any convenient route, for example, by infusion or bolus injection, by absorption through epithelial or mucocutaneous linings (e.g., oral mucosa, rectal and intestinal mucosa, etc.) and can be administered together with another therapeutic agent. Administration can be systemic or local. Various delivery systems are known, e.g., encapsulation in liposomes, microparticles, microcapsules or capsules, and can be used to administer an Organic compound. In certain embodiments, more than one Organic compound is administered to a patient.

Methods of administration include but are not limited to intradermal, intramuscular, intraperitoneal, intravenous, subcutaneous, intranasal, epidural, oral, sublingual, intranasal, intracerebral, intravaginal, transdermal, rectal, by inhalation, or topically to the ears, nose, eyes, or skin. The preferred mode of administration is left to the discretion of the practitioner, and will depend in-part upon the site of the medical condition (such as the site of cancer).

The method of administering the ubiquitin conjugating enzyme inhibiting compounds of the invention may be suitably chosen depending on the nature and/or the site of the hyperproliferative disorder to be treated. For example, it may be desirable to administer one or more compounds of the invention locally to the area in need of treatment. This can be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers. In one embodiment, administration can be by direct injection at the site (or former site) of a cancer, tumor or neoplastic or pre-neoplastic tissue.

In certain other situations, it may be desirable to administer one or more organic compounds using any suitable route, including intraventricular and intrathecal injection. Intraventricular injection may be facilitated by an intraventricular catheter, for example, attached to a reservoir, such as an Ommaya reservoir.

Pulmonary administration can also be employed, e.g. by use of an inhaler or nebulizer, and formulation with an aerosolizing agent, or via perfusion in a fluorocarbon or synthetic pulmonary surfactant. In certain embodiments, the organic compound can be formulated as a suppository, with traditional binders and carriers such as triglycerides. In another embodiment, the organic compound can be delivered in a vesicle, in particular a liposome (see Langer, Science 249: 1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another example, the compound of the invention can be delivered in a controlled-release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321: 574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228: 190 (1985); During et al., Ann. Neurol. 25:351 (1989); Howard et al., J. Neurosurg. 71:105 (1989)). In yet another embodiment, a controlled-release system can be placed in proximity of the target of the organic compound, thus requiring only a fraction of the systemic dose (see, e.g., Goodson, in Medical Applications of Controlled Release, Sahara, vol. 2, pp. 115-138 (1984)). Other controlled-release systems discussed in the review by Langer (Science 249: 1527-1533 (1990)) may be used.

The present pharmaceutical compositions contain an effective amount of an organic compound, preferably in purified form, together with a suitable amount of a pharmaceutically acceptable carrier so as to provide the form for proper administration to the patient.

The term "pharmaceutically acceptable" as referred to herein, means approved by a regulatory agency of the Federal or a state government or listed in the U.S. Pharmacopoeia or other generally recognized pharmacopoeia for use in animals, and more particularly in humans. The term "carrier" refers to a diluent, adjuvant, excipient, or vehicle with which a Organic compound is administered. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. In addition, auxiliary, stabilizing, thickening, lubricating and coloring agents may be used. When administered to a patient, compounds of the invention are preferably sterile. Water is a preferred carrier when the organic compound is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or phi buffering agents.

The present pharmaceutical compositions can be in the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable composition is a capsule comprising the compounds of the invention. Other examples of suitable pharmaceutical carriers include auxiliary agents, and exigents such as, for example, those described in "Remington's Pharmaceutical Sciences" 20th Ed. (2002).

In one embodiment, the compounds of the invention are formulated in accordance with routine procedures as a pharmaceutical composition adapted for intravenous administration to human beings. Typically, compounds of the invention for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the organic compound is to be administered by infusion, it can be dispensed, for example, with an infusion bottle containing sterile pharmaceutical grade water or saline. Where the organic compound is administered by injection, an ampoule of sterile water for injection or saline can be provided so that the ingredients may be mixed prior to administration. Compositions for oral delivery may be in the form of tablets, lozenges, aqueous or oily suspensions, granules, powders, emulsions, capsules, syrups, or elixirs, for example, orally administered compositions may contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard carriers such as mannitol, lactose, starch, magnesium stearate, sodium saccharine, cellulose, magnesium carbonate, etc. Such carriers are preferably of pharmaceutical grade.

Dosage of the Organic Compound

The amount of the organic compound that will be effective in the treatment of a particular disorder or condition will depend on the nature of the disorder or condition and can be determined by standard clinical techniques. In addition, in vitro or in vivo assays may optionally be employed to help identify optimal dosage ranges. The precise dose will also depend on the route of administration, and the seriousness of the disease or disorder, and should be decided according to the judgment of the practitioner and each patient's circumstances. However, suitable dosage ranges, particularly for intravenous administration, are generally about 20-500 micrograms of an organic compound per kilogram body weight. In specific preferred embodiments of the invention, the i.v. dose is about 10-40, 30-60, 60-100, or 100-200 micrograms per kilogram body weight. In other embodiments, the i.v. dose is about 75-150, 150-250, 250-375 or 375-500 micrograms per kilogram body weight. Suitable dosage ranges for intranasal administration are generally about 0.01 pa/kg body weight to 1 mg/kg body weight. Suppositories generally contain a organic compound in the range of about 0.5% to 10% by weight. Oral compositions preferably contain an organic compound about 10% to 95% by weight of a organic compound. In specific preferred embodiments of the invention, suitable dose ranges for oral administration are generally about 1-500 micrograms of a Organic compound per kilogram body weight. In specific preferred embodiments, the oral dose is about 1-10, 10-30, 30-90, or 90-150 micrograms per kilogram body weight.

In other embodiments, the oral dose is about 150-250, 250-325, 325-450 or 450-1000 micrograms per kilogram body weight. Effective doses may be extrapolated from dose-response curves derived from in vitro or animal model test systems. Such animal models and systems are well known in the art and are disclosed herein.

The invention also provides pharmaceutical kits comprising a container containing a organic compound. Optionally associated with such container(s) can be a notice in the form prescribed by a governmental agency regulating the manufacture, use or sale of pharmaceuticals or biological products, which notice reflects approval by the agency of manufacture, use or sale for human administration; or instructions for use. The kit can also comprise a container containing a chemotherapeutic agent useful for treating cancer or a neoplastic disease.

The compounds of the invention are preferably assayed in vitro, and then in vivo for the desired therapeutic or prophylactic activity, prior to use in humans. For example, in vitro assays can be used to determine whether administration of one or more compounds of the invention is preferred.

In one embodiment, a patient tissue sample is grown in culture, and contacted or otherwise administered with an organic compound, and the effect of such organic compound upon the tissue sample is observed and compared to a non-contacted tissue. In other embodiments, a cell-culture model is used in which the cells of the cell culture are contacted or otherwise administered with a organic compound, and the effect of such organic compound upon the cell-culture is observed and compared to a non-contacted cell culture. Generally, a lower level of proliferation or survival of the contacted cells compared to the non-contracted cells indicates that the organic compound is effective to treat the patient. Such compounds of the invention may also be demonstrated effective and safe using animal model systems.

Assays for measuring the in vitro and in vivo activity are described in Examples 2-4. Other methods will be known to the skilled artisan and are within the scope of the invention.

Combination Therapy

A hyperproliferative disorder, including but not limited to cancer or a neoplastic disease, a neoplasm, a tumor, a metastasis, or any disease or disorder characterized by uncontrolled cell growth, can be treated or prevented by administration of an effective amount of an organic compound. In one embodiment, a composition comprising an effective amount of one or more organic compounds or a pharmaceutically acceptable salt thereof, is administered. In certain embodiments, the invention encompasses methods for treating or preventing cancer or a neoplastic disease comprising administering to a patient in need thereof an effective amount of a organic compound and another therapeutic agent. In one embodiment, the therapeutic agent is a chemotherapeutic agent including, but not limited to, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel. In one embodiment, the organic compound exerts its activity at the same time the other therapeutic agent exerts its activity.

Treatable and Preventable Hyperproliferative Disorders

Hyperproliferative disorders include cancerous disease states. Cancerous disease states may be categorized as pathologic, i.e., characterizing or constituting a disease state, e.g., malignant tumor growth, or may be categorized as non-pathologic, i.e., a deviation from normal but not associated with a disease state, e.g., cell proliferation associated with wound repair. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term "carcinoma" also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In one embodiment of the invention the compounds of the invention can be used to treat or prevent a variety of hyperproliferative disorders. Preferentially, the compounds of the invention can be used to treat breast cancer, colon cancer and prostate cancer. Additional hyperproliferative disorders include but are not limited to, cancer of the head, neck, eye, skin, mouth, throat, esophagus, chest, bone, lung, colon, sigmoid, rectum, stomach, prostate, ovary, testicle, kidney, liver, pancreas, brain, intestine, heart or adrenals (for a review of such disorders, 10 see Fishman et al., 1985, Medicine, 2d Ed., J.B. Lippincott Co., Philadelphia).

Treatable and Preventable Ub Conjugating Disorders

In addition to hyperproliferative disorders, dysfunction of the ubiquitin system has also been implicated in Huntington's, Parkinson's and Alzheimer's disease (Reboud-Ravaux, M. Protein Degradation in Health and Disease. Volume 29 (Heidelberg: Springer Verlag, 2002). In one embodiment, compounds of the invention can be used to treat a Ub conjugating disorder, e.g., cancer, Huntington's, Parkinson's and Alzheimer's disease.

Parkinson's disease is a slowly progressing, degenerative nervous system disorder characterized by tremors when at rest, sluggish initiation of movements and muscle rigidity. In Parkinson's disease, nerve cells in the basal ganglia degenerate, resulting in lower production of dopamine and fewer connections with other nerve cells and muscles.

Generally, Parkinson's disease begins with a tremor in the resting hand that decreases when the hand moves purposefully and disappears during sleep. Eventually, the tremor may progress to the other hand, the arms, the legs, and effect the jaw, tongue, forehead and eyelids. Individuals with Parkinson's disease often have difficulty initiating a movement, and experience muscle stiffness. As a result of these symptoms, any type of minor physical activity becomes extremely difficult.

A variety of drugs may be used to treat Parkinson's disease. These drugs include levodopa, bromocriptine, pergolide, selegiline, anticholinergics, antihistamines, antidepressants, propranolol and amantadine. Although these drugs do not stop the progression of, or cure Parkinson' disease, they may make physical activity easier.

The mobility of a Parkinson's patient can be maintained by continuing to perform daily activities, exercising, physical therapy and the use of mechanical aids such as wheeled walkers.

Parkinson's disease is characterized by the idiopathic and progressive loss of mesencephalic dopaminergic neurons of the substantia nigra leading to a loss of dopamine in the striatura, the main projection field of these neurons. This neuronal degeneration results in the major symptoms of Parkinson's disease, i.e., tremor, muscular rigidity, difficulty in movement initiation, and loss of postural reflex (Pratt and McPherson, 1997, Cytokine and Growth Factor Reviews, 8:267-292).

Alzheimer's disease is the most common form of dementia. Although the exact cause of Alzheimer's disease is not known, genetic factors play a role in the occurrence and development of this disease. Furthermore, the ubiquitin system has been implicated in the development of Alzheimer's disease. Patient's with Alzheimer's disease suffer from degeneration of parts of the brain, resulting in the destruction of cells and the reduction of the responsiveness of the remaining cells to the chemicals that transmit signals in the brain. Abnormal tissues, termed senile plaques, neurofibrillary tangles, and abnormal proteins appear in the brain. During an autopsy, Alzheimer's disease can be diagnosed by the presence of abnormal brain tissue, characterized by a loss of nerve cells, the presence of tangles within the remaining nerve cells, and plaques made of amyloid scattered throughout the brain tissue.

The progression of Alzheimer's disease can be slowed but not stopped with a number of drugs including tacrine, and donepezil.

Dementia resulting from Alzheimer's disease normal begins subtly and results in a gradual deterioration of memory. The first sign of dementia is usually forgetfulness (Berkow et al., supra).

Alzheimer's disease (AD) is a progressive neurodegenerative disease characterized by neuronal loss primarily in the temporal lobes and neocortex. This neuronal loss causes progressive loss of cognitive function and ultimately leads to severe dementia. Histological analysis of brains from AD patients has revealed that they contain numerous neuritic plaques consisting substantially of aggregates of β amyloid peptide (Aβ, a 39-43 amino acid peptide derived from a larger transmembrane protein referred to as the amyloid precursor protein (APP). Numerous investigators have shown that Aβ is neurotoxic in vitro and in vivo, which has led to the conclusion that Aβ accumulation is a key factor in the development of AD. The cause of increased accumulation of Aβ in the brains of AD patients is not known but is believed to be a consequence of increased production of APP and/or abnormal processing of the protein ultimately leading to elevated levels of Aβ.

The suitability of the compounds of the invention for treatment of Huntington's, Parkinson's and Alzheimer's disease can be assessed in any of a number of animal models. For example, animal models for Huntington's disease (see, e.g., Mangiarini et al., 1996, Cell 87: 493-506, Lin et al., 2001, Hum. Mol. Genet. 10: 137-144), Alzheimer's disease (Hsiao, 1998, Exp. Gerontol. 33: 883-889; Hsiao et al., 1996, Science 274: 99-102), Parkinson's disease (Kim et al., 2002, Nature 418: 50-56) are known and can also be used to evaluate the efficacy of compounds of the invention.

Animals administered the compounds are evaluated for symptoms relative to animals not administered the compounds. A change in the severity of symptoms (e.g., a 10% or greater improvement in one or more symptoms), or a delay in the onset of symptoms, in treated versus untreated animals is indicative of therapeutic efficacy.

EXAMPLES

Example 1

Identification of Ubc Inhibitors by Structure Based Screening

A structure based screening assay was performed on yeast Ubc4 to identify compounds that bind to the active sites of these molecules. 3-D coordinates for yeast Ubc4 (PDB ID No. 1QCQ) were entered into the InsightII program (InsightII, Accelrys, Inc., San Diego, Calif.). Calculations were performed on the molecule to identify the active sites. Yeast Ubc4 active sites identified with the InsightII program included amino acids Lys64, Pro66, Lys67, Ile68, Asn84, Ile85, Leu90, Lys91 and Leu120. Similarly, another identified active site included amino acids Pro65, Pro66, Lys67, Ile68, Asn84, Leu90, Lys91 and Leu120 of S. cerevisiae Ubc4. Active sites in human UbcSa included Lys66, Ile67, Ala68, Ser83, Cys85, Leu86, Leu89 and Arg90 of SEQ ID NO:2 and Pro64, Pro65, Lys66, Ile67, Ser83, Ile84, Cys85, Leu86, Leu89, Arg90 and Leu119 of SEQ ID NO:2. Active sites in S. cerevisiae Ubc7 included Pro68, Lys70, Tyr83, Glu87, Val88, Cys89, Leu93 and His94 of SEQ ID NO:3; and Pro68, Pro69, Lys70, Leu71, Tyr83, Glu87, Val88, Cys89, Leu93 and His94 of SEQ ID NO:3.

After identifying the active sites a screen for identifying binding compounds was performed with the LUDI program using compounds contained in the Available Chemical Directory (ACD). The ACD was converted to a LUDI compatible library using the Genfra program and hydrogens were added to all compounds of the library. The center of search for the LUDI run was defined based upon active sites. A search radius of 9-12 Å was chosen for the different E2s. In LUDI, a rigid body protein-ligand docking method was used to reduce time, and a standard protonation states at pH 7.0 was used for all Ubcs/E2s and ligands.

LUDI identified numerous binding compounds which were scored by the Boehm scoring function (Boehm, 1998). The highest scoring compounds were manually selected to remove those that protruded from the binding site, displaying hydrophobic moieties pointing into solution. Additionally only those that formed at least two hydrogen bonds with a good contact score were selected. FIG. 1 shows the binding interaction between yeast Ubc4 and one of the compounds identified by the screen (HBS01). HBS01 was found to interact with Pro66, Ile85 and Leu90 of SEQ ID NO:1. Compound OBWP was found to interact with Pro66, Ile68, Leu90 and Lys91 of SEQ ID NO:1. Compound 05RB was found to interact with Ile67 and Leu89 of SEQ ID NO:2. Compound 0464 was found to interact with Pro65, Ile67, and Ser 83 of SEQ ID NO:2. Compound OC7K was found to interact with Glu87, Val88, Leu93 and His94 of SEQ ID NO:3. Compound 8EAG was found to interact with Pro69, Leu71 and Val88 of SEQ ID NO:3. HBS01 was further evaluated by in vivo and in vitro assays as described herein.

Example 2

Figure 2:
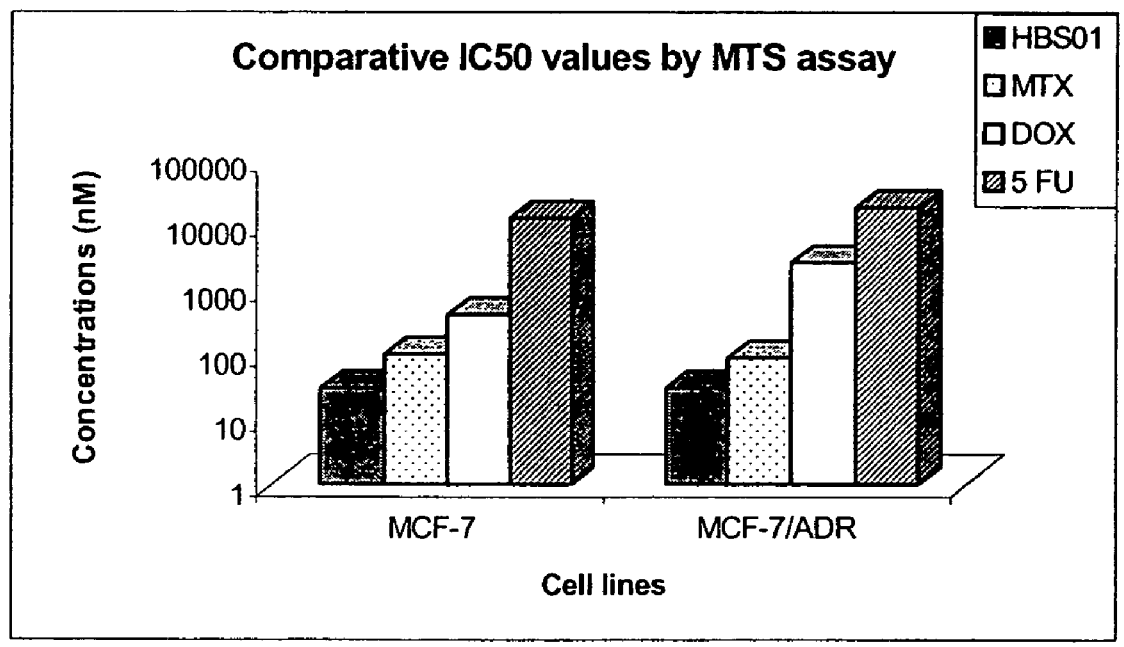
FIG. 2 shows the results from Example 2 measuring IC50 values. The bar graph indicates the IC50 values as determined by an MTS assay for HBS01, MTX, DOX and 5FU in MCF-7 and MCF-7-Adr. IC50 concentrations are indicated on the y-axis in nM concentrations.

Determination of IC50 Values for HBS01 in the Breast Cell Lines MCF-7 and MCF-7-Adr In order to determine the IC50 values of HBS01 an MTS assay was performed on MCF-7 and MCF-7/ADR (adramycin resistance) cell lines. Cells were plated in a 96 well plate at 5,000 cells/well. After plating, cells were treated for 96 hours with either HBS01, methotrexate (MTX), doxyrubicin (DOX), or 5-Fluorouracil (5FU) and an MTS assay was performed according to manufacturer's protocol with the CELL TITER 96 AQ non-radioactive cell proliferation assay kit (Promega, Cat. No. G5421). Viable cells were quantitated based on absorbance at 490 nm. IC50 values for HBS01, MTX, DOX and 5FU are shown in FIG. 2. The results indicated that HBS01 had an IC50 value of 30 nM in MCF-7 and MCF-7Adr. Thus, HBS01 was an extremely potent inhibitor of MCF-7 and MCF-7Adr proliferation.

Example 3

Effect of HBS01 in C85 Colorectal Tumors in Mice

C85 human colorectal cancer cell growth was assessed in nude mice (NIH, Cr:(MCr)-Fox1nu(nu/nu homogygous), Taconic Inc., Germantown, N.Y.) treated or pretreated with HBS01 over a 19 day period. Briefly, pretreated animals were administered three daily doses of HBS01 at 17 mg/Kg given on day −3, −2, and −1 prior to tumor cell injection on day 0. No further treatment was given to the pretreated animals. Nude mice were injected in the flanks with 1 million C85 human colorectal cancer cells. Treated animals were treated with daily injections of HBS01 at 17 mg/kg per at days 10, 11, 12, 15, 16 and 17 following appearance of palpable tumors on day 10.

Figure 3:
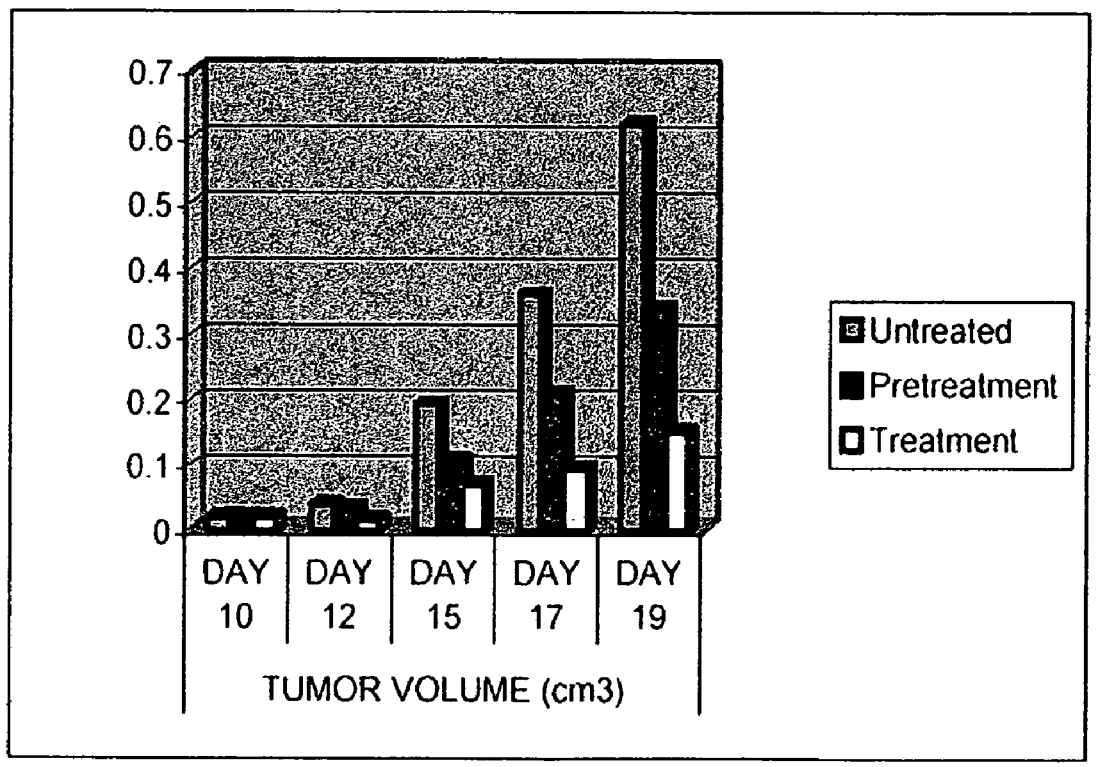
FIG. 3 shows the results from Example 3 measuring tumor volume. The bar graph indicates the tumor volume on day 10, 12, 15, 17 and 19 in untreated, pretreated (HBS01) and treated (HBS01) mice injected with C85 colorectal adenocarcinoma tumor cells. Tumor volume is indicated on the y-axis in $cm^3$.

Tumor diameters were measured with calipers every alternate day and tumor volumes were calculated by $\frac{1}{2}ab^2$ where a is the larger diameter (Friedman, H S., et al. Cancer Res. 46, 2827-2833). The results are shown in FIG. 3 as tumor volume in cm$^3$. The results indicated that treatment with HBS01 significantly inhibited the growth of established tumors in animals treated with HBS01. Additionally, pretreating mice with HBS01 delayed tumor growth.

Example 4

Effect of HBS01 in MCF-7 Breast Cancer Tumors in Mice

Figure 4:
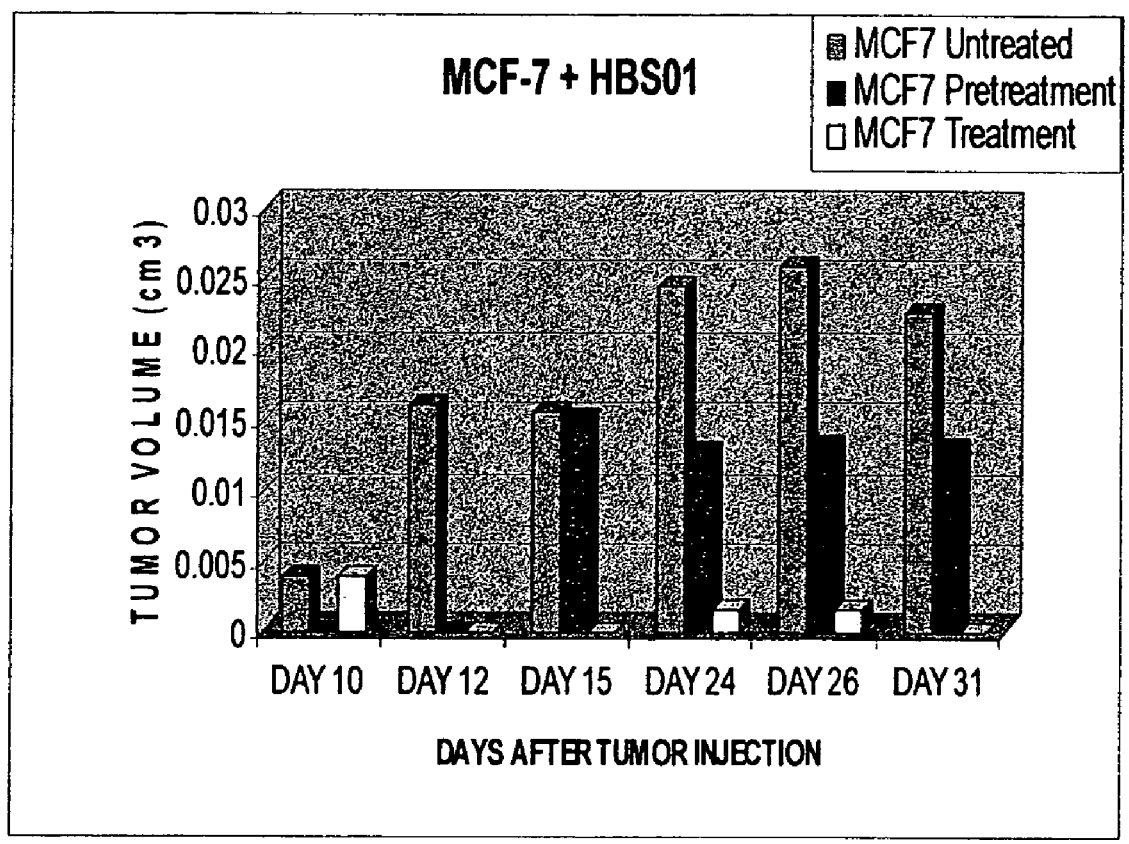
FIG. 4 shows the results from Example 4 measuring tumor volume. The bar graph indicates the tumor volume on day 10, 12, 15, 24, 26 and 31 in untreated, pretreated (HBS01) and treated (HBS01) mice injected MCF-7 breast cancer tumors. Tumor volume is indicated on the y-axis in $cm^3$.

MCF-7 breast cancer cell growth was assessed in nude mice (NIH, Cr:(MCr)-Fox1nu(nu/nu homogygous), Taconic Inc., Germantown, N.Y.) treated or pretreated with HBS01 over 31 days. Briefly, pretreated animals were administered three daily doses of HBS01 at 17 mg/Kg given on day −3, −2, and −1 prior to tumor cell injection on day 0. No further treatment was given to the pretreated animals. Nude mice were injected in the flanks with 200,000 MCF-7 breast cancer cells. Treated animals were treated with daily injections of HBS01 at 17 mg/kg per at days 10, 11, 12, 15, 16 and 17 following appearance of palpable tumors on day 10. Tumor diameters were measured with calipers every alternate day and tumor volumes were calculated by $\frac{1}{2}ab^2$ where a is the larger diameter (Friedman, H S., et al. Cancer Res. 46, 2827-2833). The results are shown in FIG. 4 as tumor volume in cm$^3$. The results showed that HBS01 significantly inhibited tumor growth in animals treated with HBS01 following MCF-7 palpable tumors. Additionally, pretreating mice with HBS01 delayed the onset of MCF-7 tumors.

Example 5

Clonogenic Assays

Compounds identified by structure based screening were assayed in a clonogenic assay with C85 colorectal adenocarcinoma cells. Briefly, C85 cells were plated at 200 cells per well in six well plates. Seventy-two hours after plating, compounds 05RB, 0BWP, 0FZK, 0RZL, HBS01, 01LX, 0464, 1BJO AND 27NT were added at various concentrations (See Table 1). Colonies were counted 96 hours after treatment and IC50 concentrations determined (Table 1). Results indicate that many of the compounds identified by structure based screening were effective at inhibiting C85 tumor cell growth.

TABLE 1

CLONOGENIC ASSAY OF COLON C85s WITH Ubc/E2 INHIBITORS

| Compound | ID No. | CONCENTRATIONS (µM) | | | | | | | Target | IC-50 |
|---|---|---|---|---|---|---|---|---|---|---|
| N-Phenyl-4-phenylenediamine | 05RB | 0 | 625 | 312 | 156 | 78 | 39 | 19.5 9.7 | Ubc5a | 37.5 |
| 2-Chloro-4-nitrobenzamide | 0BWP | 0 | 2000 | 1500 | 1000 | 750 | 500 | | Ubc4 | 600 |
| 5-chloro-2,3-dihydroxypyridine | 0FZK | 0 | 400 | 250 | 150 | 75 | 15 | | Ubc3 | 175 |
| 1-Phenyl-4-methyl-3-pyrazolidone | 0RZL | 0 | 70 | 35 | 15 | 7.5 | 3.75 | | Ubc3 | 50 |
| 4-(Aminomethyl)piperidine | HBS01* | 0 | 100 | 50 | 25 | 12.5 | 6.25 | | Ubc4/ Ubc1 | 30 nM* |
| 2-Acetamidophenol | 01LX | 0 | 500 | 400 | 300 | 150 | 50 | | Ubc3 | 375 |
| 6-AMINOINDAZOLE | 0464 | 0 | 1300 | 650 | 300 | 150 | 75 | | Ubc5a | 70 |
| 2-ethylformanilide | 1BJO | 0 | 200 | 150 | 100 | 50 | 25 | | Ubc5a | Non toxic |
| 4-(Methylamino)pyridine | 27NT | 0 | 700 | 350 | 175 | 75 | 15 | | Ubc4 | Non toxic |

*denotes nM

Example 6

Effect of HBS01 on Metastatic Cancer Growth

The effect of HBS01 on the metastatic growth of enhanced green fluorescent protein (EGFP) marked C85 cells was assayed in nude mice (NIH, Cr:(MCr)-Fox1nu(nu/nu homogygous), Taconic Inc., Germantown, N.Y.). Briefly, nude mice were pre-treated with 14.5 mg/kg of HBS01 every 24 hrs for five days. At the completion of pre-treatment the pre-treated or control non-treated mice were injected in the tail vein with $1 \times 10^6$ EGFP marked C85 cells. Ten days post-C85 injection, the mice were dissected and tumor size assessed based on intravital fluorescence imaging and liver biopsies. Results indicated that metastatic tumors were not detectable in pre-treated mice compared with controls.

Example 7

Selective Targeting by HBS01

The ability of HBS01 to specifically inhibit selected protein ubiquination pathways was assayed in C85 cell lines. Briefly, C85 cells were plated at 200 cells per well in six well plates.

Cells were either untreated (controls) or treated for 24 or 48 hrs with HBS01. After the treatment period, cells were harvested and extracts were prepared from the cells by freeze fracturing in liquid nitrogen in breakage buffer (50 mM Tris pH 7.5, 1 mM DTT, "Complete" protease inhibitor cocktail (Roche, Cat.# 1697498), 10 µM MG132). Roughly 300 mg of total protein extracts in 300 µl of breakage buffer was supplemented with 20 µg of PHH-Ub (HA and His6 tagged Ubiquitin) and incubated at 30° C. for 60 min. 3×SDS-PAGE sample buffer was added to 40 µl of this reaction and boiled for 3 min. The extracts were run on 12% Laemmli gels that were either stained with Coomassie Blue R-250 or blotted with HRP conjugated 12CA5 monoclonal antibody (Roche, Inc., Indianapolis, Ind.) and visualized by ECL, with the ECL plus western blot detection kit (Amersham Biosciences, Piscataway, N.J.) according to manufacturers instructions.

Figure 5:
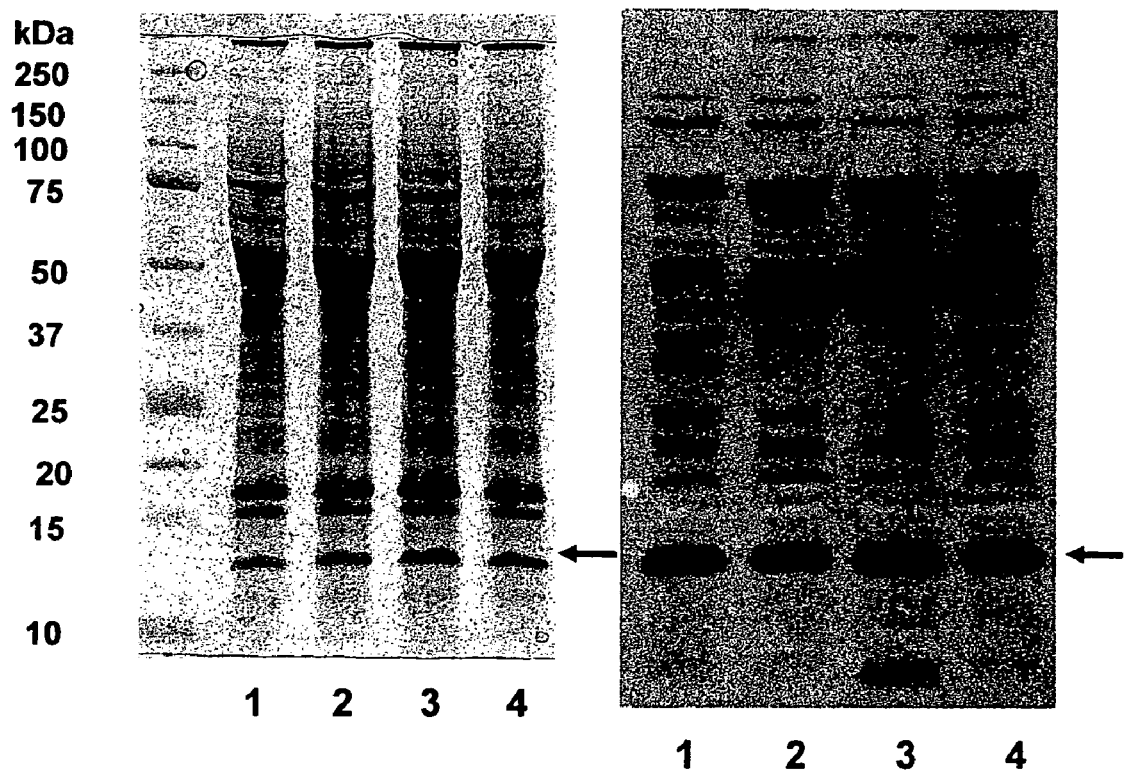
FIG. 5 shows the results from Example 7 measuring protein ubiquination in control and HBS01 treated cells. The gels were 12% Laemmli gels. The gel on the left panel was stained with Commassie Blue R-250 and the gel on the right panel is a Western Blot utilizing the 12CA5 monoclonal antibody specific for the HA-tagged ubiquitin proteins. Lane 1 depicts cell lysates from cells treated with HBS01 for 24 hrs; Lane 2 depicts cell lysates from cells untreated for 24 hrs; Lane 3 depicts cell lysates from cells treated with HBS01 for 48 hrs; and Lane 4 depicts cell lysates from cells untreated for 48 hrs.

As seen in FIG. 5, results indicated that control and treated cell lysates had similar ubiquitin intensities and banding patterns. This demonstrated that general inactivation of the ubiquitin conjugation pathways did not occur with HBS01 treatment.

Example 8

Blockage of Ubiquination and Accumulation of Cyclin-B by HBS01

The ability of HBS01 to inhibit protein ubiquination of cyclin-B was assayed in C85 cell lines. Briefly, C85 cells were plated at 200 cells per well in six well plates. Cells were either untreated (controls) or treated for 24 hrs with HBS01. After the treatment period, cells were harvested and extracts were prepared from the cells by freeze fracturing in liquid nitrogen in breakage buffer (50 mM Tris pH 7.5, 1 mM DTT, "Complete" protease inhibitor cocktail (Roche, Cat.# 1697498), 10 µM MG132). Roughly 300 mg of total protein extracts in 300 µl of breakage buffer was supplemented with 20 µg of PHH-Ub (HA and His6 tagged Ubiquitin) and incubated at 30° C. for 60 min. 3×SDS-PAGE sample buffer was added to 40 µl of this reaction and boiled for 3 min. The extracts were run on 12% Laemmli gels and Western Blots were performed with anti-cyclin-B antibody (Santa Cruz Biotechnology, Inc., Santa Cruz, Calif.). Results were visualized by ECL, with the ECL plus western blot detection kit (Amersham Biosciences, Piscataway, N.J.) according to manufacturers instructions.

Figure 6:
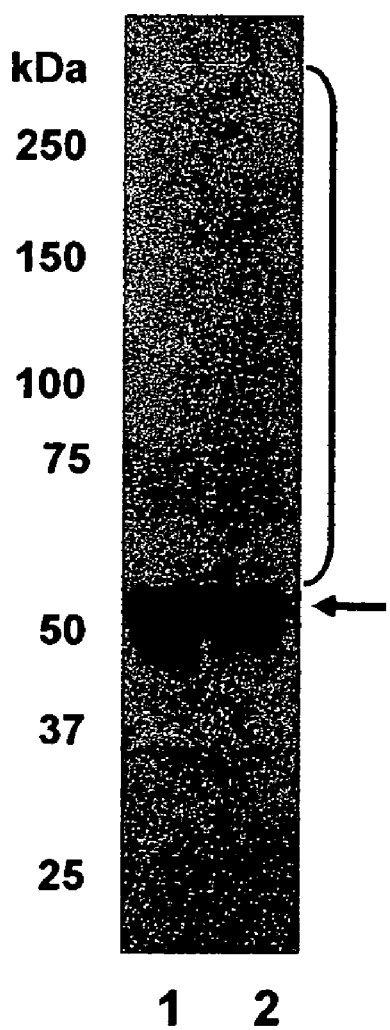
FIG. 6 shows the results from Example 8 measuring protein ubiquination in control and HBS01 treated cells. The results were analyzed on a 12% Laemmli gel Western blotted with anti-cyclin-b. Lane 1 depicts cell lysates from cells treated with HBS01 for 24 hrs while Lane 2 depicts cell lysates from cells untreated for 24 hrs. The arrow indicates non-ubiquinated cyclin-B.

The results are shown in FIG. 6. The data indicated that a smear of ubiquinated cyclin-B is absent in control cell lysates but present in the lysates of cells treated with HBS01. Thus, cyclin-B accumulates in cells treated with HBS01. These results indicate that HBS01 selectively inhibited the ubiquination of cyclin-B.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

---

I claim:

1. A method of determining a selective interaction between an ubiquitin conjugating enzyme (Ubc) and an organic compound comprising the steps of:
   a) inputting 3-D co-ordinates of a fragment of the ubiquitin conjugating enzyme into an electronic storage medium, wherein said fragment is less than the complete 3-D co-ordinates of said ubiquitin conjugating enzyme, using refined homology modeling or the crystal structure of said ubiquitin conjugating enzyme;
   b) determining a catalytic active site capable of forming a thioester adduct with ubiquitin in said fragment of the ubiquitin conjugating enzyme; wherein said catalytic active site encompasses a region on said ubiquitin conjugating enzyme within a 20 Angstrom radius of the catalytic cysteine of said ubiquitin conjugating enzyme;
   c) simulating a binding interaction between said active site in the fragment of the ubiquitin conjugating enzyme and a modified library of organic compounds, wherein said modified library of organic compounds is a library of organic compounds which have been altered by protonation to include hydrogens;
   d) identifying compounds in said library of organic compounds that interact with said active site in said fragment of step (c) of the ubiquitin conjugating enzyme, and
   e) then manually selecting the highest scored compounds and eliminating those compounds which excessively protrude out of the binding site, as visualized by the computer 3-D structure of the Ubc with the docked organic compound, one compound at a time.

2. The method of claim 1, wherein said ubiquitin conjugating enzyme is selected from the group consisting of: Ubc1, Ubc2, Ubc3, Ubc4, Ubc5, Ubc6, Ubc7, Ubc8, Ubc10, Ubc11, and Ubc13.

3. The method of claim 2, wherein said ubiquitin conjugating enzyme is a yeast ubiquitin conjugating enzyme or a mouse, rat, or human homolog.

4. The method of claim 1, wherein said atomic 3-D coordinates are selected from the group consisting of: 1AYZ, 1A3S, 1QCQ, 2UCZ, 1I7K 1J7D, 1JAT, and 1JBB.

5. The method of claim 1, wherein step (b) is performed by a molecular topology and charge visualization program.

6. The method of claim 1, wherein said step (c) is performed with LUDI.

7. The method of claim 1, wherein said library of organic compounds is are the compounds listed in the Available Chemicals Directory.

8. The method of claim 1, wherein said active site comprises the amino acid residues corresponding to Lys64, Pro66, Lys67, Ile68, Asn84, Ile85, Leu90, Lys91 and Leu120 of SEQ ID NO:1.

9. The method of claim 1, wherein said active site comprises the amino acid residues corresponding to Pro65, Pro66, Lys67, Ile68, Asn84, Leu90, Lys91 and Leu120 of SEQ ID NO:1.

10. The method of claim 1, wherein said active site comprises the amino acid residues corresponding to Lys66, Ile67, Ala68, Ser83, Cys85, Leu86, Leu89 and Arg90 of SEQ ID NO:2.

11. The method of claim 1, wherein said active site comprises the amino acid residues corresponding to Pro64, Pro65, Lys66, Ile67, Ser83, Ile84, Cys85, Leu86, Leu89, Arg90 and Leu119 of SEQ ID NO:2.

12. A method of determining a selective interaction between an ubiquitin conjugating enzyme and an organic compound, wherein said ubiquitin conjugating enzyme is Ubc5, and wherein said method comprises the steps of:
   a) inputting 3-D co-ordinates of a fragment of the ubiquitin conjugating enzyme into an electronic storage medium, using refined homology modeling, wherein said fragment is less than the complete 3-D co-ordinates of said ubiquitin conjugating enzyme or the crystal structure of said ubiquitin conjugating enzyme;
   b) determining a catalytic active site capable of forming a thioester adduct with ubiquitin in said fragment of the ubiquitin conjugating enzyme, wherein said catalytic active site encompasses a region on said ubiquitin conjugating enzyme within a 20 Angstrom radius of the catalytic cysteine of said ubiquitin conjugating enzyme;
   c) simulating a binding interaction between said active sites in said fragment of the ubiquitin conjugating enzyme and a library of organic compounds;
   d) identifying compounds in said library of organic compounds that interact with said active sites in said fragment of the ubiquitin conjugating enzyme, and
   e) then manually selecting the highest scored compounds and eliminating those compounds which excessively protrude out of the binding site, as visualized by the computer 3-D structure of the Ubc with the docked said organic compound, one compound at a time.

13. The method of claim 12, wherein said Ubc5 ubiquitin conjugating enzyme is a mouse, rat, or human homolog of Ubc5.

14. The method of claim 1 or 12, wherein the active site is a region on said ubiquitin conjugating enzyme within a 20 Angstrom radius of the catalytic cysteine of said ubiquitin conjugating enzyme.

* * * * *

SEQUENCE LISTING

<160> NUMBER OF SEQ ID NOS: 3

<210> SEQ ID NO 1
<211> LENGTH: 148
<212> TYPE: PRT
<213> ORGANISM: Saccharomyces cerevisiae

<400> SEQUENCE: 1

```
Met Ser Ser Ser Lys Arg Ile Ala Lys Glu Leu Ser Asp Leu Glu Arg
1               5                   10                  15

Asp Pro Pro Thr Ser Cys Ser Ala Gly Pro Val Gly Asp Asp Leu Tyr
            20                  25                  30

His Trp Gln Ala Ser Ile Met Gly Pro Ala Asp Ser Pro Tyr Ala Gly
        35                  40                  45

Gly Val Phe Phe Leu Ser Ile His Phe Pro Thr Asp Tyr Pro Phe Lys
    50                  55                  60
```

```
Pro Pro Lys Ile Ser Phe Thr Thr Lys Ile Tyr His Pro Asn Ile Asn
 65                  70                  75                  80

Ala Asn Gly Asn Ile Cys Leu Asp Ile Leu Lys Asp Gln Trp Ser Pro
                 85                  90                  95

Ala Leu Thr Leu Ser Lys Val Leu Leu Ser Ile Cys Ser Leu Leu Thr
            100                 105                 110

Asp Ala Asn Pro Asp Asp Pro Leu Val Pro Glu Ile Ala His Ile Tyr
            115                 120                 125

Lys Thr Asp Arg Pro Lys Tyr Glu Ala Thr Ala Arg Glu Trp Thr Lys
130                 135                 140

Lys Tyr Ala Val
145

<210> SEQ ID NO 2
<211> LENGTH: 147
<212> TYPE: PRT
<213> ORGANISM: Homo sapiens

<400> SEQUENCE: 2

Met Ala Leu Lys Arg Ile Gln Lys Glu Leu Ser Asp Leu Gln Arg Asp
 1               5                  10                  15

Pro Pro Ala His Cys Ser Ala Gly Pro Val Gly Asp Asp Leu Phe His
                 20                  25                  30

Trp Gln Ala Thr Ile Met Gly Pro Pro Asp Ser Ala Tyr Gln Gly Gly
            35                  40                  45

Val Phe Phe Leu Thr Val His Phe Pro Thr Asp Tyr Pro Phe Lys Pro
         50                  55                  60

Pro Lys Ile Ala Phe Thr Thr Lys Ile Tyr His Pro Asn Ile Asn Ser
 65                  70                  75                  80

Asn Gly Ser Ile Cys Leu Asp Ile Leu Arg Ser Gln Trp Ser Pro Ala
                 85                  90                  95

Leu Thr Val Ser Lys Val Leu Leu Ser Ile Cys Ser Leu Leu Cys Asp
            100                 105                 110

Pro Asn Pro Asp Asp Pro Leu Val Pro Asp Ile Ala Gln Ile Tyr Lys
            115                 120                 125

Ser Asp Lys Glu Lys Tyr Asn Arg His Ala Arg Glu Trp Thr Gln Lys
130                 135                 140

Tyr Ala Met
145

<210> SEQ ID NO 3
<211> LENGTH: 165
<212> TYPE: PRT
<213> ORGANISM: Saccharomyces cerevisiae

<400> SEQUENCE: 3

Met Ser Lys Thr Ala Gln Lys Arg Leu Leu Lys Glu Leu Gln Gln Leu
 1               5                  10                  15

Ile Lys Asp Ser Pro Pro Gly Ile Val Ala Gly Pro Lys Ser Glu Asn
                 20                  25                  30

Asn Ile Phe Ile Trp Asp Cys Leu Ile Gln Gly Pro Asp Thr Pro
            35                  40                  45

Tyr Ala Asp Gly Val Phe Asn Ala Lys Leu Glu Phe Pro Lys Asp Tyr
         50                  55                  60

Pro Leu Ser Pro Pro Lys Leu Thr Phe Thr Pro Ser Ile Leu His Pro
 65                  70                  75                  80
```

-continued

```
Asn Ile Tyr Pro Asn Gly Glu Val Cys Ile Ser Ile Leu His Ser Pro
                85                  90                  95

Gly Asp Asp Pro Asn Met Tyr Glu Leu Ala Glu Glu Arg Trp Ser Pro
            100                 105                 110

Val Gln Ser Val Glu Lys Ile Leu Leu Ser Val Met Ser Met Leu Ser
        115                 120                 125

Glu Pro Asn Ile Glu Ser Gly Ala Asn Ile Asp Ala Cys Ile Leu Trp
    130                 135                 140

Arg Asp Asn Arg Pro Glu Phe Glu Arg Gln Val Lys Leu Ser Ile Leu
145                 150                 155                 160

Lys Ser Leu Gly Phe
            165
```